(12) United States Patent
Villani, Jr. et al.

(10) Patent No.: US 10,088,452 B2
(45) Date of Patent: Oct. 2, 2018

(54) METHOD FOR DETECTING DEFECTS IN CONDUCTIVE MATERIALS BASED ON DIFFERENCES IN MAGNETIC FIELD CHARACTERISTICS MEASURED ALONG THE CONDUCTIVE MATERIALS

(71) Applicant: Lockheed Martin Corporation, Bethesda, MD (US)

(72) Inventors: Joseph A. Villani, Jr., Moorsetown, NJ (US); John B. Stetson, Jr., New Hope, PA (US)

(73) Assignee: LOCKHEED MARTIN CORPORATION, Bethesda, MD (US)

( * ) Notice: Subject to any disclaimer, the term of this patent is extended or adjusted under 35 U.S.C. 154(b) by 0 days.

(21) Appl. No.: 15/003,145

(22) Filed: Jan. 21, 2016

(65) Prior Publication Data
US 2017/0199156 A1    Jul. 13, 2017

Related U.S. Application Data

(60) Provisional application No. 62/277,657, filed on Jan. 12, 2016.

(51) Int. Cl.
*G01N 27/82* (2006.01)
(52) U.S. Cl.
CPC .................................... *G01N 27/82* (2013.01)
(58) Field of Classification Search
CPC ........ G01N 27/82; G01N 17/02; G01N 27/85; G01N 17/00; G01N 2021/8861; G01N 2021/8864; G01N 27/83; G01N 27/902; G01N 2223/316; G01N 2223/646; G01N 23/18; G01N 27/904; G01N 33/20; G01V 3/081; G01V 3/08; G01V 3/30; G01V 3/15; G01R 33/02; G01R 33/032; G01R 27/20;
(Continued)

(56) References Cited

U.S. PATENT DOCUMENTS 2,746,027 A    5/1956   Murray
3,359,812 A    12/1967  Everitt
(Continued)

FOREIGN PATENT DOCUMENTS

CN    105738845 A    7/2016
DE    69608006 T2    2/2001
(Continued)

OTHER PUBLICATIONS

Brenneis, et al. "Ultrafast electronic readout of diamond nitrogen-vacancy centres coupled to graphene." Nature nanotechnology 10.2 (2015): 135-139.
(Continued)

*Primary Examiner* — Vinh Nguyen
(74) *Attorney, Agent, or Firm* — Foley & Lardner LLP

(57) ABSTRACT

A method includes passing a magnetometer along a length of a material. The method also includes measuring, via the magnetometer, a first magnetic field magnitude along a first portion of the length of the material and measuring, via the magnetometer, a second magnetic field magnitude along a second portion of the length of material. The method further includes determining that the material includes a defect along the second portion of the length of material by determining that the first magnetic field magnitude is different than the second magnetic field magnitude.

15 Claims, 5 Drawing Sheets

(58) Field of Classification Search
CPC ............ G01R 33/0029; G01R 33/0206; G01R 33/022; G01R 33/0327; G01R 33/04; G06F 3/0346; G06F 3/04842
See application file for complete search history.

(56) References Cited

U.S. PATENT DOCUMENTS

| | | | |
|---|---|---|---|
| 3,389,333 A | 6/1968 | Wolff et al. | |
| 3,490,032 A | 1/1970 | Zurflueh | |
| 3,514,723 A | 5/1970 | Cutler | |
| 3,518,531 A | 6/1970 | Huggett | |
| 3,621,380 A | 11/1971 | Carl, Jr. | |
| 3,745,452 A | 7/1973 | Osburn et al. | |
| 3,899,758 A | 8/1975 | Maier et al. | |
| 4,025,873 A | 5/1977 | Chilluffo | |
| 4,078,247 A | 3/1978 | Albrecht | |
| 4,084,215 A | 4/1978 | Willenbrock | |
| 4,322,769 A | 3/1982 | Cooper | |
| 4,329,173 A | 5/1982 | Culling | |
| 4,359,673 A | 11/1982 | Bross et al. | |
| 4,368,430 A | 1/1983 | Dale et al. | |
| 4,410,926 A | 10/1983 | Hafner et al. | |
| 4,437,533 A | 3/1984 | Bierkarre et al. | |
| 4,514,083 A | 4/1985 | Fukuoka | |
| 4,588,993 A | 5/1986 | Babij et al. | |
| 4,636,612 A | 1/1987 | Cullen | |
| 4,638,324 A | 1/1987 | Hannan | |
| 4,675,522 A | 6/1987 | Arunkumar | |
| 4,768,962 A | 9/1988 | Kupfer et al. | |
| 4,818,990 A | 4/1989 | Fernandes | |
| 4,820,986 A | 4/1989 | Mansfield et al. | |
| 4,945,305 A | 7/1990 | Blood | |
| 4,958,328 A | 9/1990 | Stubblefield | |
| 4,982,158 A * | 1/1991 | Nakata .................. | G01N 27/82 324/248 |
| 5,019,721 A | 5/1991 | Martens et al. | |
| 5,038,103 A | 8/1991 | Scarzello et al. | |
| 5,113,136 A | 5/1992 | Hayashi et al. | |
| 5,134,369 A | 7/1992 | Lo et al. | |
| 5,189,368 A | 2/1993 | Chase | |
| 5,200,855 A | 4/1993 | Meredith et al. | |
| 5,245,347 A | 9/1993 | Bonta et al. | |
| 5,252,912 A | 10/1993 | Merritt et al. | |
| 5,301,096 A | 4/1994 | Klontz et al. | |
| 5,384,109 A | 1/1995 | Klaveness et al. | |
| 5,396,802 A | 3/1995 | Moss | |
| 5,420,549 A | 5/1995 | Prestage | |
| 5,425,179 A | 6/1995 | Nickel et al. | |
| 5,427,915 A | 6/1995 | Ribi et al. | |
| 5,548,279 A | 8/1996 | Gaines | |
| 5,568,516 A | 10/1996 | Strohallen et al. | |
| 5,586,069 A | 12/1996 | Dockser | |
| 5,597,762 A | 1/1997 | Popovici et al. | |
| 5,638,472 A | 6/1997 | Van Delden | |
| 5,694,375 A | 12/1997 | Woodall | |
| 5,719,497 A | 2/1998 | Veeser et al. | |
| 5,731,996 A | 3/1998 | Gilbert | |
| 5,764,061 A | 6/1998 | Asakawa et al. | |
| 5,818,352 A | 10/1998 | McClure | |
| 5,846,708 A | 12/1998 | Hollis et al. | |
| 5,888,925 A | 3/1999 | Smith et al. | |
| 5,907,420 A | 5/1999 | Chraplyvy et al. | |
| 5,907,907 A | 6/1999 | Ohtomo et al. | |
| 5,915,061 A | 6/1999 | Vanoli | |
| 6,042,249 A | 3/2000 | Spangenberg | |
| 6,057,684 A | 5/2000 | Murakami et al. | |
| 6,124,862 A | 9/2000 | Boyken et al. | |
| 6,130,753 A | 10/2000 | Hopkins et al. | |
| 6,144,204 A | 11/2000 | Sementchenko | |
| 6,195,231 B1 | 2/2001 | Sedlmayr et al. | |
| 6,215,303 B1 * | 4/2001 | Weinstock ............. | G01N 27/82 324/248 |
| 6,360,173 B1 | 3/2002 | Fullerton | |
| 6,398,155 B1 | 6/2002 | Hepner et al. | |
| 6,433,944 B1 | 8/2002 | Nagao et al. | |
| 6,472,651 B1 | 10/2002 | Ukai | |
| 6,472,869 B1 | 10/2002 | Upschulte et al. | |
| 6,504,365 B2 | 1/2003 | Kitamura | |
| 6,542,242 B1 | 4/2003 | Yost et al. | |
| 6,621,578 B1 | 9/2003 | Mizoguchi | |
| 6,636,146 B1 | 10/2003 | Wehoski | |
| 6,686,696 B2 | 2/2004 | Mearini et al. | |
| 6,690,162 B1 | 2/2004 | Schopohl et al. | |
| 6,765,487 B1 | 7/2004 | Holmes et al. | |
| 6,788,722 B1 | 9/2004 | Kennedy et al. | |
| 6,809,829 B1 | 10/2004 | Takata et al. | |
| 7,118,657 B2 | 10/2006 | Golovchenko et al. | |
| 7,221,164 B1 | 5/2007 | Barringer | |
| 7,277,161 B2 | 10/2007 | Claus | |
| 7,305,869 B1 | 12/2007 | Berman et al. | |
| 7,307,416 B2 | 12/2007 | Islam et al. | |
| RE40,343 E | 5/2008 | Anderson | |
| 7,400,142 B2 | 7/2008 | Greelish | |
| 7,413,011 B1 | 8/2008 | Chee et al. | |
| 7,427,525 B2 | 9/2008 | Santori et al. | |
| 7,448,548 B1 | 11/2008 | Compton | |
| 7,471,805 B2 | 12/2008 | Goldberg | |
| 7,474,090 B2 | 1/2009 | Islam et al. | |
| 7,543,780 B1 | 6/2009 | Marshall et al. | |
| 7,546,000 B2 | 6/2009 | Spillane et al. | |
| 7,570,050 B2 | 8/2009 | Sugiura | |
| 7,608,820 B1 | 10/2009 | Berman et al. | |
| 7,705,599 B2 | 4/2010 | Strack et al. | |
| 7,805,030 B2 | 9/2010 | Bratkovski et al. | |
| 7,868,702 B2 | 1/2011 | Ohnishi | |
| 7,889,484 B2 * | 2/2011 | Choi ....................... | H05K 5/02 312/223.1 |
| 7,916,489 B2 | 3/2011 | Okuya | |
| 7,983,812 B2 | 7/2011 | Potter | |
| 8,022,693 B2 | 9/2011 | Meyersweissflog | |
| 8,120,351 B2 | 2/2012 | Rettig et al. | |
| 8,120,355 B1 | 2/2012 | Stetson | |
| 8,124,296 B1 | 2/2012 | Fischel | |
| 8,138,756 B2 | 3/2012 | Barclay et al. | |
| 8,193,808 B2 | 6/2012 | Fu et al. | |
| 8,294,306 B2 | 10/2012 | Kumar et al. | |
| 8,310,251 B2 * | 11/2012 | Orazem .................. | C23F 13/04 324/713 |
| 8,311,767 B1 | 11/2012 | Stetson | |
| 8,334,690 B2 | 12/2012 | Kitching et al. | |
| 8,415,640 B2 | 4/2013 | Babinec et al. | |
| 8,471,137 B2 | 6/2013 | Adair et al. | |
| 8,480,653 B2 | 7/2013 | Birchard et al. | |
| 8,525,516 B2 | 9/2013 | Le Prado et al. | |
| 8,547,090 B2 | 10/2013 | Lukin et al. | |
| 8,574,536 B2 | 11/2013 | Boudou et al. | |
| 8,575,929 B1 | 11/2013 | Wiegert | |
| 8,686,377 B2 | 4/2014 | Twitchen et al. | |
| 8,758,509 B2 | 6/2014 | Twitchen et al. | |
| 8,803,513 B2 | 8/2014 | Hosek et al. | |
| 8,854,839 B2 | 10/2014 | Cheng et al. | |
| 8,885,301 B1 | 11/2014 | Heidmann | |
| 8,913,900 B2 | 12/2014 | Lukin et al. | |
| 8,933,594 B2 | 1/2015 | Kurs | |
| 8,947,080 B2 | 2/2015 | Lukin et al. | |
| 8,963,488 B2 | 2/2015 | Campanella et al. | |
| 9,103,873 B1 | 8/2015 | Martens et al. | |
| 9,157,859 B2 | 10/2015 | Walsworth et al. | |
| 9,245,551 B2 | 1/2016 | El Hallak et al. | |
| 9,249,526 B2 | 2/2016 | Twitchen et al. | |
| 9,291,508 B1 | 3/2016 | Biedermann et al. | |
| 9,369,182 B2 | 6/2016 | Kurs et al. | |
| 9,442,205 B2 | 9/2016 | Geiser et al. | |
| 9,541,610 B2 | 1/2017 | Kaup et al. | |
| 9,551,763 B1 | 1/2017 | Hahn et al. | |
| 9,557,391 B2 | 1/2017 | Egan et al. | |
| 9,570,793 B2 | 2/2017 | Borodulin | |
| 9,590,601 B2 | 3/2017 | Krause et al. | |
| 9,614,589 B1 | 4/2017 | Russo et al. | |
| 9,645,223 B2 | 5/2017 | Megdal et al. | |
| 9,680,338 B2 | 6/2017 | Malpas et al. | |
| 9,689,679 B2 | 6/2017 | Budker et al. | |
| 9,720,055 B1 | 8/2017 | Hahn et al. | |
| 9,778,329 B2 | 10/2017 | Heidmann | |

(56) References Cited

U.S. PATENT DOCUMENTS

| | | |
|---|---|---|
| 2002/0144093 A1 | 10/2002 | Inoue et al. |
| 2002/0167306 A1 | 11/2002 | Zalunardo et al. |
| 2003/0058346 A1 | 3/2003 | Bechtel et al. |
| 2003/0076229 A1 | 4/2003 | Blanpain et al. |
| 2003/0098455 A1 | 5/2003 | Amin et al. |
| 2003/0235136 A1 | 12/2003 | Akselrod et al. |
| 2004/0013180 A1 | 1/2004 | Giannakis et al. |
| 2004/0022179 A1 | 2/2004 | Giannakis et al. |
| 2004/0042150 A1 | 3/2004 | Swinbanks et al. |
| 2004/0081033 A1 | 4/2004 | Arieli et al. |
| 2004/0109328 A1 | 6/2004 | Dahl et al. |
| 2004/0247145 A1 | 12/2004 | Luo et al. |
| 2005/0031840 A1 | 2/2005 | Swift et al. |
| 2005/0068249 A1 | 3/2005 | Du Toit et al. |
| 2005/0099177 A1 | 5/2005 | Greelish |
| 2005/0112594 A1 | 5/2005 | Grossman |
| 2005/0126905 A1 | 6/2005 | Golovchenko et al. |
| 2005/0130601 A1 | 6/2005 | Palermo et al. |
| 2005/0134257 A1 | 6/2005 | Etherington et al. |
| 2005/0138330 A1 | 6/2005 | Owens et al. |
| 2005/0146327 A1 | 7/2005 | Jakab |
| 2006/0012385 A1 | 1/2006 | Tsao et al. |
| 2006/0054789 A1 | 3/2006 | Miyamoto et al. |
| 2006/0055584 A1 | 3/2006 | Waite et al. |
| 2006/0062084 A1 | 3/2006 | Drew |
| 2006/0071709 A1 | 4/2006 | Maloberti et al. |
| 2006/0245078 A1 | 11/2006 | Kawamura |
| 2006/0247847 A1 | 11/2006 | Carter et al. |
| 2006/0255801 A1 | 11/2006 | Ikeda |
| 2006/0291771 A1 | 12/2006 | Braunisch et al. |
| 2007/0004371 A1 | 1/2007 | Okanobu |
| 2007/0247147 A1 | 10/2007 | Xiang et al. |
| 2007/0273877 A1 | 11/2007 | Kawano et al. |
| 2008/0016677 A1 | 1/2008 | Creighton, IV |
| 2008/0048640 A1 | 2/2008 | Hull et al. |
| 2008/0078233 A1 | 4/2008 | Larson et al. |
| 2008/0089367 A1 | 4/2008 | Srinivasan et al. |
| 2008/0204004 A1 | 8/2008 | Anderson |
| 2008/0217516 A1 | 9/2008 | Suzuki et al. |
| 2008/0239265 A1 | 10/2008 | Den Boef |
| 2008/0253264 A1 | 10/2008 | Nagatomi et al. |
| 2008/0266050 A1 | 10/2008 | Crouse et al. |
| 2008/0299904 A1 | 12/2008 | Yi et al. |
| 2009/0015262 A1 | 1/2009 | Strack et al. |
| 2009/0042592 A1 | 2/2009 | Cho et al. |
| 2009/0058697 A1 | 3/2009 | Aas et al. |
| 2009/0060790 A1 | 3/2009 | Okaguchi et al. |
| 2009/0079417 A1 | 3/2009 | Mort et al. |
| 2009/0079426 A1 | 3/2009 | Anderson |
| 2009/0132100 A1 | 5/2009 | Shibata |
| 2009/0157331 A1 | 6/2009 | Van Netten |
| 2009/0161264 A1 | 6/2009 | Meyersweissflog |
| 2009/0195244 A1 | 8/2009 | Mouget et al. |
| 2009/0222208 A1 | 9/2009 | Speck |
| 2009/0277702 A1 | 11/2009 | Kanada et al. |
| 2009/0310650 A1 | 12/2009 | Chester et al. |
| 2010/0004802 A1 | 1/2010 | Bodin et al. |
| 2010/0015438 A1 | 1/2010 | Williams et al. |
| 2010/0015918 A1 | 1/2010 | Liu et al. |
| 2010/0045269 A1 | 2/2010 | Lafranchise et al. |
| 2010/0071904 A1 | 3/2010 | Burns et al. |
| 2010/0102809 A1 | 4/2010 | May |
| 2010/0134922 A1 | 6/2010 | Yamada et al. |
| 2010/0157305 A1 | 6/2010 | Henderson |
| 2010/0188081 A1 | 7/2010 | Lammegger |
| 2010/0237149 A1 | 9/2010 | Olmstead |
| 2010/0271016 A1 | 10/2010 | Barclay et al. |
| 2010/0277121 A1 | 11/2010 | Hall et al. |
| 2010/0308813 A1 | 12/2010 | Lukin et al. |
| 2010/0315079 A1 | 12/2010 | Lukin et al. |
| 2010/0321117 A1 | 12/2010 | Gan |
| 2010/0326042 A1 | 12/2010 | McLean et al. |
| 2011/0034393 A1 | 2/2011 | Justen et al. |
| 2011/0059704 A1 | 3/2011 | Norimatsu et al. |
| 2011/0062957 A1 | 3/2011 | Fu et al. |
| 2011/0063957 A1 | 3/2011 | Isshiki et al. |
| 2011/0066379 A1 | 3/2011 | Mes |
| 2011/0120890 A1 | 5/2011 | MacPherson et al. |
| 2011/0127999 A1 | 6/2011 | Lott et al. |
| 2011/0165862 A1 | 7/2011 | Yu et al. |
| 2011/0176563 A1 | 7/2011 | Friel et al. |
| 2011/0243267 A1 | 10/2011 | Won et al. |
| 2011/0270078 A1 | 11/2011 | Wagenaar et al. |
| 2011/0315988 A1 | 12/2011 | Yu et al. |
| 2012/0016538 A1 | 1/2012 | Waite et al. |
| 2012/0019242 A1 | 1/2012 | Hollenberg et al. |
| 2012/0037803 A1 | 2/2012 | Strickland |
| 2012/0044014 A1 | 2/2012 | Stratakos et al. |
| 2012/0051996 A1 | 3/2012 | Scarsbrook et al. |
| 2012/0063505 A1 | 3/2012 | Okamura et al. |
| 2012/0087449 A1 | 4/2012 | Ling et al. |
| 2012/0089299 A1 | 4/2012 | Breed |
| 2012/0140219 A1 | 6/2012 | Cleary |
| 2012/0181020 A1 | 7/2012 | Barron et al. |
| 2012/0194068 A1 | 8/2012 | Cheng et al. |
| 2012/0203086 A1 | 8/2012 | Rorabaugh et al. |
| 2012/0232838 A1 | 9/2012 | Kemppi et al. |
| 2012/0235633 A1 | 9/2012 | Kesler et al. |
| 2012/0235634 A1 | 9/2012 | Hall et al. |
| 2012/0245885 A1 | 9/2012 | Kimishima |
| 2012/0257683 A1 | 10/2012 | Schwager et al. |
| 2012/0281843 A1 | 11/2012 | Christensen et al. |
| 2012/0326793 A1 | 12/2012 | Gan |
| 2013/0043863 A1 | 2/2013 | Ausserlechner et al. |
| 2013/0093424 A1 | 4/2013 | Blank et al. |
| 2013/0127518 A1 | 5/2013 | Nakao |
| 2013/0179074 A1 | 7/2013 | Haverinen |
| 2013/0215712 A1 | 8/2013 | Geiser et al. |
| 2013/0223805 A1 | 8/2013 | Ouyang et al. |
| 2013/0265042 A1 | 10/2013 | Kawabata et al. |
| 2013/0265782 A1 | 10/2013 | Barrena et al. |
| 2013/0270991 A1 | 10/2013 | Twitchen et al. |
| 2013/0279319 A1 | 10/2013 | Matozaki et al. |
| 2014/0012505 A1 | 1/2014 | Smith et al. |
| 2014/0037932 A1 | 2/2014 | Twitchen et al. |
| 2014/0044208 A1 | 2/2014 | Woodsum |
| 2014/0061510 A1 | 3/2014 | Twitchen et al. |
| 2014/0070622 A1 | 3/2014 | Keeling et al. |
| 2014/0072008 A1 | 3/2014 | Faraon et al. |
| 2014/0077231 A1 | 3/2014 | Twitchen et al. |
| 2014/0081592 A1 | 3/2014 | Bellusci et al. |
| 2014/0104008 A1 | 4/2014 | Gan |
| 2014/0126334 A1 | 5/2014 | Megdal et al. |
| 2014/0139322 A1 | 5/2014 | Wang et al. |
| 2014/0154792 A1 | 6/2014 | Moynihan et al. |
| 2014/0159652 A1 | 6/2014 | Hall et al. |
| 2014/0166904 A1 | 6/2014 | Walsworth et al. |
| 2014/0167759 A1 | 6/2014 | Pines et al. |
| 2014/0168174 A1 | 6/2014 | Idzik et al. |
| 2014/0180627 A1 | 6/2014 | Naguib et al. |
| 2014/0191139 A1 | 7/2014 | Englund |
| 2014/0191752 A1 | 7/2014 | Walsworth et al. |
| 2014/0198463 A1 | 7/2014 | Klein |
| 2014/0210473 A1 | 7/2014 | Campbell et al. |
| 2014/0215985 A1 | 8/2014 | Pollklas |
| 2014/0225606 A1 | 8/2014 | Endo et al. |
| 2014/0247094 A1 | 9/2014 | Englund et al. |
| 2014/0265555 A1 | 9/2014 | Hall et al. |
| 2014/0272119 A1 | 9/2014 | Kushalappa et al. |
| 2014/0273826 A1 | 9/2014 | Want et al. |
| 2014/0291490 A1 | 10/2014 | Hanson et al. |
| 2014/0297067 A1 | 10/2014 | Malay |
| 2014/0306707 A1 | 10/2014 | Walsworth et al. |
| 2014/0327439 A1 | 11/2014 | Cappellaro et al. |
| 2014/0335339 A1 | 11/2014 | Dhillon et al. |
| 2014/0340085 A1 | 11/2014 | Cappellaro et al. |
| 2014/0368191 A1 | 12/2014 | Goroshevskiy et al. |
| 2015/0001422 A1 | 1/2015 | Englund et al. |
| 2015/0009746 A1 | 1/2015 | Kucsko et al. |
| 2015/0018018 A1 | 1/2015 | Shen et al. |
| 2015/0022404 A1 | 1/2015 | Chen et al. |
| 2015/0048822 A1 | 2/2015 | Walsworth et al. |
| 2015/0054355 A1 | 2/2015 | Ben-Shalom et al. |
| 2015/0061590 A1 | 3/2015 | Widmer et al. |

(56) References Cited

U.S. PATENT DOCUMENTS

| | | |
|---|---|---|
| 2015/0090033 A1 | 4/2015 | Budker et al. |
| 2015/0128431 A1 | 5/2015 | Kuo |
| 2015/0137793 A1 | 5/2015 | Englund et al. |
| 2015/0153151 A1 | 6/2015 | Kochanski |
| 2015/0192532 A1 | 7/2015 | Clevenson et al. |
| 2015/0192596 A1 | 7/2015 | Englund et al. |
| 2015/0225052 A1 | 8/2015 | Cordell |
| 2015/0235661 A1 | 8/2015 | Heidmann |
| 2015/0253355 A1 | 9/2015 | Grinolds et al. |
| 2015/0268373 A1 | 9/2015 | Meyer |
| 2015/0269957 A1 | 9/2015 | El Hallak et al. |
| 2015/0276897 A1 | 10/2015 | Leussler et al. |
| 2015/0288352 A1 | 10/2015 | Krause et al. |
| 2015/0299894 A1 | 10/2015 | Markham et al. |
| 2015/0303333 A1 | 10/2015 | Yu et al. |
| 2015/0314870 A1 | 11/2015 | Davies |
| 2015/0326030 A1 | 11/2015 | Malpas et al. |
| 2015/0326410 A1 | 11/2015 | Krause et al. |
| 2015/0374250 A1 | 12/2015 | Hatano et al. |
| 2015/0377865 A1 | 12/2015 | Acosta et al. |
| 2015/0377987 A1 | 12/2015 | Menon et al. |
| 2016/0018269 A1 | 1/2016 | Maurer et al. |
| 2016/0031339 A1 | 2/2016 | Geo |
| 2016/0036529 A1 | 2/2016 | Griffith et al. |
| 2016/0052789 A1 | 2/2016 | Gaathon et al. |
| 2016/0054402 A1 | 2/2016 | Meriles |
| 2016/0071532 A9 | 3/2016 | Heidmann |
| 2016/0077167 A1 | 3/2016 | Heidmann |
| 2016/0097702 A1 | 4/2016 | Zhao et al. |
| 2016/0113507 A1 | 4/2016 | Reza et al. |
| 2016/0139048 A1 | 5/2016 | Heidmann |
| 2016/0146904 A1 | 5/2016 | Stetson et al. |
| 2016/0161429 A1 | 6/2016 | Englund et al. |
| 2016/0214714 A1 | 7/2016 | Sekelsky |
| 2016/0216304 A1 | 7/2016 | Sekelsky |
| 2016/0216340 A1 | 7/2016 | Egan et al. |
| 2016/0216341 A1 | 7/2016 | Boesch et al. |
| 2016/0221441 A1 | 8/2016 | Hall et al. |
| 2016/0223621 A1 | 8/2016 | Kaup et al. |
| 2016/0231394 A1 | 8/2016 | Manickam et al. |
| 2016/0266220 A1 | 9/2016 | Sushkov et al. |
| 2016/0282427 A1 | 9/2016 | Heidmann |
| 2016/0291191 A1 | 10/2016 | Fukushima et al. |
| 2016/0313408 A1 | 10/2016 | Hatano et al. |
| 2016/0348277 A1 | 12/2016 | Markham et al. |
| 2016/0356863 A1 | 12/2016 | Boesch et al. |
| 2017/0010214 A1 | 1/2017 | Osawa et al. |
| 2017/0010334 A1 | 1/2017 | Krause et al. |
| 2017/0010338 A1 | 1/2017 | Bayat et al. |
| 2017/0010594 A1 | 1/2017 | Kottapalli et al. |
| 2017/0023487 A1 | 1/2017 | Boesch |
| 2017/0030982 A1 | 2/2017 | Jeske et al. |
| 2017/0038314 A1 | 2/2017 | Suyama et al. |
| 2017/0068012 A1 | 3/2017 | Fisk |
| 2017/0074660 A1 | 3/2017 | Gann et al. |
| 2017/0075020 A1 | 3/2017 | Gann et al. |
| 2017/0104426 A1 | 4/2017 | Mills |
| 2017/0138735 A1 | 5/2017 | Cappellaro et al. |
| 2017/0199156 A1 | 7/2017 | Villani et al. |
| 2017/0205526 A1 | 7/2017 | Meyer |
| 2017/0207823 A1 | 7/2017 | Russo et al. |
| 2017/0211947 A1 | 7/2017 | Fisk |
| 2017/0212046 A1 | 7/2017 | Cammerata |
| 2017/0212177 A1 | 7/2017 | Coar et al. |
| 2017/0212178 A1 | 7/2017 | Hahn et al. |
| 2017/0212179 A1 | 7/2017 | Hahn et al. |
| 2017/0212180 A1 | 7/2017 | Hahn et al. |
| 2017/0212181 A1 | 7/2017 | Coar et al. |
| 2017/0212182 A1 | 7/2017 | Hahn et al. |
| 2017/0212183 A1 | 7/2017 | Egan et al. |
| 2017/0212184 A1 | 7/2017 | Coar et al. |
| 2017/0212185 A1 | 7/2017 | Hahn et al. |
| 2017/0212186 A1 | 7/2017 | Hahn et al. |
| 2017/0212187 A1 | 7/2017 | Hahn et al. |
| 2017/0212190 A1 | 7/2017 | Reynolds et al. |
| 2017/0212258 A1 | 7/2017 | Fisk |

FOREIGN PATENT DOCUMENTS

| | | |
|---|---|---|
| DE | 19600241 C2 | 8/2002 |
| DE | 10228536 A1 | 1/2003 |
| EP | 0 161 940 B1 | 12/1990 |
| EP | 0 718 642 | 6/1996 |
| EP | 0 726 458 | 8/1996 |
| EP | 1 505 627 | 2/2005 |
| EP | 1 685 597 | 8/2006 |
| EP | 1 990 313 | 11/2008 |
| EP | 2 163 392 | 3/2010 |
| EP | 2 495 166 A1 | 9/2012 |
| EP | 2 587 232 A1 | 5/2013 |
| EP | 2 705 179 | 3/2014 |
| EP | 2 707 523 | 3/2014 |
| EP | 2 745 360 | 6/2014 |
| EP | 2 769 417 | 8/2014 |
| EP | 2 790 031 | 10/2014 |
| EP | 2 837 930 | 2/2015 |
| EP | 2 907 792 | 8/2015 |
| GB | 2 433 737 | 7/2007 |
| GB | 2423366 A | 8/2008 |
| GB | 2 482 596 | 2/2012 |
| GB | 2 483 767 | 3/2012 |
| GB | 2 486 794 | 6/2012 |
| GB | 2 490 589 | 11/2012 |
| GB | 2 491 936 | 12/2012 |
| GB | 2 493 236 | 1/2013 |
| GB | 2 495 632 A | 4/2013 |
| GB | 2 497 660 | 6/2013 |
| GB | 2 510 053 A | 7/2014 |
| GB | 2 515 226 | 12/2014 |
| GB | 2 522 309 | 7/2015 |
| GB | 2 526 639 | 12/2015 |
| JP | 3782147 B2 | 6/2006 |
| JP | 4800896 B2 | 10/2011 |
| JP | 2012-103171 | 5/2012 |
| JP | 2012-110489 | 6/2012 |
| JP | 2012-121748 | 6/2012 |
| JP | 2013-028497 | 2/2013 |
| JP | 5476206 B2 | 4/2014 |
| JP | 5522606 B2 | 6/2014 |
| JP | 5536056 B2 | 7/2014 |
| JP | 5601183 B2 | 10/2014 |
| JP | 2014-215985 | 11/2014 |
| JP | 2014-216596 | 11/2014 |
| JP | 2015-518562 A | 7/2015 |
| JP | 5764059 B2 | 8/2015 |
| JP | 2015-167176 | 9/2015 |
| JP | 2015-529328 | 10/2015 |
| JP | 5828036 B2 | 12/2015 |
| JP | 5831947 B2 | 12/2015 |
| WO | WO-87/04028 A1 | 7/1987 |
| WO | WO-88/04032 A1 | 6/1988 |
| WO | WO-95/33972 A1 | 12/1995 |
| WO | WO-2011/046403 A2 | 4/2011 |
| WO | WO-2011/153339 | 12/2011 |
| WO | WO-2012/016977 A2 | 2/2012 |
| WO | WO-2012/084750 | 6/2012 |
| WO | WO-2013/059404 A1 | 4/2013 |
| WO | WO-2013/066446 A1 | 5/2013 |
| WO | WO-2013/066448 | 5/2013 |
| WO | WO-2013/093136 A1 | 6/2013 |
| WO | WO-2013/188732 A1 | 12/2013 |
| WO | WO-2013/190329 A1 | 12/2013 |
| WO | WO-2014/011286 A2 | 1/2014 |
| WO | WO-2014/099110 A2 | 6/2014 |
| WO | WO-2014/135544 A1 | 9/2014 |
| WO | WO-2014/135547 A1 | 9/2014 |
| WO | WO-2014/166883 A1 | 10/2014 |
| WO | WO-2014/210486 A1 | 12/2014 |
| WO | WO-2015/015172 A1 | 2/2015 |
| WO | WO-2015/142945 | 9/2015 |
| WO | WO-2015/157110 | 10/2015 |
| WO | WO-2015/157290 | 10/2015 |

(56) References Cited

FOREIGN PATENT DOCUMENTS

| | | |
|---|---|---|
| WO | WO-2015/158383 A1 | 10/2015 |
| WO | WO-2015/193156 A1 | 12/2015 |
| WO | WO-2016/075226 A1 | 5/2016 |
| WO | WO-2016/118756 | 7/2016 |
| WO | WO-2016/118791 | 7/2016 |
| WO | WO-2016/122965 | 8/2016 |
| WO | WO-2016/122966 | 8/2016 |
| WO | WO-2016/126435 | 8/2016 |
| WO | WO-2016/126436 | 8/2016 |
| WO | WO-2016/190909 | 12/2016 |
| WO | WO-2017/007513 | 1/2017 |
| WO | WO-2017/007514 | 1/2017 |
| WO | WO-2017/014807 | 1/2017 |
| WO | PCT/US2017/021593 | 3/2017 |
| WO | PCT/US2017/021811 | 3/2017 |
| WO | PCT/US2017/022118 | 3/2017 |
| WO | PCT/US2017/022279 | 3/2017 |
| WO | PCT/US2017/024165 | 3/2017 |
| WO | PCT/US2017/024167 | 3/2017 |
| WO | PCT/US2017/024168 | 3/2017 |
| WO | PCT/US2017/024169 | 3/2017 |
| WO | PCT/US2017/024171 | 3/2017 |
| WO | PCT/US2017/024172 | 3/2017 |
| WO | PCT/US2017/024173 | 3/2017 |
| WO | PCT/US2017/024174 | 3/2017 |
| WO | PCT/US2017/024175 | 3/2017 |
| WO | PCT/US2017/024177 | 3/2017 |
| WO | PCT/US2017/024179 | 3/2017 |
| WO | PCT/US2017/024180 | 3/2017 |
| WO | PCT/US2017/024181 | 3/2017 |
| WO | PCT/US2017/024182 | 3/2017 |
| WO | WO-2017/039747 | 3/2017 |
| WO | PCT/US2017/035315 | 5/2017 |
| WO | WO-2017/095454 A1 | 6/2017 |
| WO | WO-2017/127079 A1 | 7/2017 |
| WO | WO-2017/127080 A1 | 7/2017 |
| WO | WO-2017/127081 A1 | 7/2017 |
| WO | WO-2017/127085 A1 | 7/2017 |
| WO | WO-2017/127090 A1 | 7/2017 |
| WO | WO-2017/127091 A1 | 7/2017 |
| WO | WO-2017/127093 A1 | 7/2017 |
| WO | WO-2017/127094 A1 | 7/2017 |
| WO | WO-2017/127095 A1 | 7/2017 |
| WO | WO-2017/127096 A1 | 7/2017 |
| WO | WO-2017/127097 A1 | 7/2017 |
| WO | WO-2017/127098 A1 | 7/2017 |

OTHER PUBLICATIONS

Chavez, et al. "Detecting Arctic oil spills with NMR: a feasibility study." Near Surface Geophysics 13.4 (Feb. 2015): 409-416.
Dale, et al. "Medical applications of diamond magnetometry: commercial viability." arXiv preprint arXiv:1705.01994 (May 8, 2017), pp. 1-7.
Fologea, et al. "Detecting single stranded DNA with a solid state nanopore." Nano Letters 5.10 (Aug. 15, 2005): 1905-1909.
Gaebel, et al. "Room-temperature coherent coupling of single spins in diamond." Nature Physics 2.6 (May 28, 2006): 408-413.
Heerema, et al. "Graphene nanodevices for DNA sequencing." Nature nanotechnology 11.2 (Feb. 3, 2016): 127-136.
International Search Report and Written Opinion of the International Searching Authority dated Apr. 4, 2017 from related PCT application PCT/US16/68366, 9 pages.
International Search Report and Written Opinion of the International Searching Authority dated Mar. 13, 2017 from related PCT application PCT/US2016/68320, 10 pages.
International Search Report and Written Opinion of the International Searching Authority dated Mar. 27, 2017 from related PCT application PCT/US16/68344, 6 pages.
International Search Report and Written Opinion of the International Searching Authority dated Mar. 31, 2017 from related PCT application PCT/US2016/066566, 11 pages.
International Search Report and Written Opinion of the International Searching Authority dated May 10, 2017 from related PCT application PCT/US17/19411, 8 pages.
International Search Report and Written Opinion of the International Searching Authority dated May 18, 2017, from related PCT application PCT/US2017/021593, 10 pages.
International Search Report and Written Opinion of the International Searching Authority dated May 19, 2017, from related PCT application PCT/US17/18099, 16 pages.
International Search Report and Written Opinion of the International Searching Authority dated May 3, 2017 from related PCT application PCT/US2017/018701, 8 pages.
International Search Report and Written Opinion of the International Searching Authority dated May 4, 2017 from related PCT application PCT/US2017/018709, 8 pages.
International Search Report and Written Opinion of the International Searching Authority dated May 8, 2017 from related PCT application PCT/US2017/17321, 17 pages.
Keyser "Enhancing nanopore sensing with DNA nanotechnology." Nature nanotechnology 11.2 (Feb. 2016): 106-108.
Lindsay "The promises and challenges of solid-state sequencing." Nature nanotechnology 11.2 (Feb. 2016): 109-111.
Matlashov, et al. "SQUIDs for magnetic resonance imaging at ultra-low magnetic field." PIERS online 5.5 (2009): 466-470.
Matlashov, et al. "SQUIDs vs. induction coils for ultra-low field nuclear magnetic resonance: experimental and simulation comparison." IEEE Transactions on Applied Superconductivity 21.3 (Jan. 1, 2012): 465-468.
Moessle, et al. "SQUID-detected magnetic resonance imaging in microtesla fields." Annu. Rev. Biomed. Eng. 9 (May 23, 2008): 389-413.
Pelliccione, et al., Two-dimensional nanoscale imaging of gadolinium spins via scanning probe relaxometry with a single spin in diamond, Phys. Rev. Applied 2.5, (Sep. 8, 2014): 054014 pp. 1-17.
Qiu et al., "Low-field NMR Measurement Procedure when SQUID Detection is Used," IEEE/CSC & ESAS European Superconductivity News Forum, No. 5, Jul. 2008.
Qiu, et al. "SQUID-detected NMR in Earth's magnetic field." Journal of Physics: Conference Series. vol. 97. No. 1. IOP Publishing, Mar. 2008, pp. 1-7.
Steinert et al., "Magnetic spin imaging under ambient conditions with sub-cellular resolution." Nature Comms 4:1607 (Mar. 19, 2013).
Sushkov, et al. "All-optical sensing of a single-molecule electron spin." Nano letters 14.11 (Nov. 7, 2013): 6443-6448.
Tetienne, et al. "Spin relaxometry of single nitrogen-vacancy defects in diamond nanocrystals for magnetic noise sensing." Physical Review B 87.23 (Apr. 3, 2013): 235436-1-235436-5.
U.S. Notice of Allowance dated Mar. 15, 2017, from related U.S. Appl. No. 15/351,862, 6 pages.
U.S. Notice of Allowance dated May 26, 2017 from related U.S. Appl. No. 15/218,821, 7 pages.
U.S. Office Action dated Apr. 17, 2017, from related U.S. Appl. No. 15/003,558, 12 pages.
U.S. Office Action dated Mar. 1, 2017, from related U.S. Appl. No. 15/003,634, 7 pages.
U.S. Office Action dated Mar. 16, 2017, from related U.S. Appl. No. 15/218,821, 7 pages.
U.S. Office Action dated May 22, 2017, from related U.S. Appl. No. 15/003,206, 12 pages.
Wells, et al. "Assessing graphene nanopores for sequencing DNA." Nano letters 12.8 (Jul. 10, 2012): 4117-4123.
Wysocki et al., "Modified Walsh-Hadamard sequences for DS CDMA wireless systems." Int. J. Adaptive Control and Signal Processing 16(8): 589-602 (Oct. 2002; first published online Sep. 23, 2002), 25 pages.
International Search Report and Written Opinion from related PCT application PCT/US2017/035315 dated Aug. 24, 2017, 7 pages.
Ramsey, et al., "Phase Shifts in the Molecular Beam Method of Separated Oscillating Fields", Physical Review, vol. 84, No. 3, Nov. 1, 1951, pp. 506-507.
U.S. Notice of Allowance on U.S. Appl. No. 14/676,740 dated Sep. 1, 2017, 7 pages.

(56) References Cited

OTHER PUBLICATIONS

U.S. Notice of Allowance on U.S. Appl. No. 15/003,206 dated Sep. 18, 2017, 11 pages.
U.S. Notice of Allowance on U.S. Appl. No. 15/003,281 dated Sep. 26, 2017, 7 pages.
U.S. Notice of Allowance on U.S. Appl. No. 15/476,636 dated Sep. 14, 2017, 10 pages.
U.S. Office Action on U.S. Appl. No. 15/003,176 dated Sep. 27, 2017, 8 pages.
U.S. Office Action on U.S. Appl. No. 15/003,292 dated Sep. 8, 2017, 8 pages.
Bucher et al, "High Resolution Magnetic Resonance Spectroscopy Using Solid-State Spins", May 25, 2017, downloaded from https://arxiv.org/ (arXiv.org > quant-ph > arXiv:1705.08887) on May 25, 2017, pp. 1-24.
International Search Report and Written Opinion of the International Searching Authority dated Jun. 1, 2017, from related PCT application PCT/US17/21811, 9 pages.
International Search Report and Written Opinion of the International Searching Authority dated Jun. 1, 2017, in related PCT application PCT/US17/22279, 20 pages.
International Search Report and Written Opinion of the International Searching Authority dated Jun. 15, 2017, from related PCT application PCT/US2017/024175, 10 pages.
International Search Report and Written Opinion of the International Searching Authority dated Jun. 9, 2017, from related patent application PCT/US2017/024181, 13 pages.
International Search Report and Written Opinion of the International Searching Authority dated Jun. 9, 2017, from related PCT application PCT/US2017/024179, 9 pages.
International Search Report and Written Opinion of the International Searching Authority dated Jul. 14, 2017, from related PCT application PCT/US2017/022118, 13 pages.
International Search Report and Written Opinion of the International Searching Authority dated Jul. 17, 2017, from related PCT application PCT/US2017/024177, 11 pages.
International Search Report and Written Opinion of the International Searching Authority dated Jul. 18, 2017, from related PCT application PCT/US2017/024167, 11 pages.
International Search Report and Written Opinion of the International Searching Authority dated Jul. 18, 2017, from related PCT application PCT/US2017/024173, 13 pages.
International Search Report and Written Opinion of the International Searching Authority dated Jul. 19, 2017, from related PCT application PCT/US2017/024171, 12 pages.
International Search Report and Written Opinion of the International Searching Authority dated Jun. 15, 2017, from related PCT application PCT/US2017/024182, 21 pages.
International Search Report and Written Opinion of the International Searching Authority dated Jun. 22, 2017, in related PCT application PCT/US2017/024180, 10 pages.
International Search Report and Written Opinion of the International Searching Authority dated Jun. 5, 2017, from related PCT application PCT/US2017/024169, 11 pages.
International Search Report and Written Opinion of the International Searching Authority dated Jun. 5, 2017, from related PCT application PCT/US2017/024174, 8 pages.
International Search Report and Written Opinion of the International Searching Authority dated Jun. 5, 2017, in related PCT application PCT/US2017/024168, 7 pages.
International Search Report and Written Opinion of the International Searching Authority dated Jun. 6, 2017, from related PCT application PCT/2017/024165, 9 pages.
International Search Report and Written Opinion of the International Searching Authority dated Jun. 6, 2017, from related PCT application PCT/US2017/024172, 9 pages.
Michaelovich et al., "Polarization Dependencies of the Nitrogen-Vacancy Center." Undergraduate Project Report, Ben-Gurion University, Aug. 2015, pp. 1-9.
Notice of Allowance dated Jun. 8, 2017, from related U.S. Appl. No. 15/351,862, 7 pages.
Sheinker et al., "Localization in 3-D Using Beacons of Low Frequency Magnetic Field." IEEE Transactions on Instrumentation and Measurement 62(12): 3194-3201 (Dec. 2013), 8 pages.
U.S. Notice of Allowance dated Aug. 11, 2017 from related U.S. Appl. No. 15/003,558, 5 pages.
U.S. Notice of Allowance dated Jul. 18, 2017 from related U.S. Appl. No. 15/003,634, 6 pages.
U.S. Notice of Allowance dated Jul. 24, 2017 from related U.S. Appl. No. 15/003,088, 12 pages.
U.S. Notice of Allowance dated Jun. 20, 2017, from related U.S. Appl. No. 15/204,675, 9 pages.
U.S. Notice of Allowance dated Jun. 28, 2017 from related U.S. Appl. No. 15/003,256, 10 pages.
U.S. Office Action dated Aug. 15, 2017 from related U.S. Appl. No. 15/003,281, 12 pages.
U.S. Office Action dated Jul. 27, 2017 from related U.S. Appl. No. 15/003,577, 15 pages.
U.S. Office Action dated Jun. 1, 2017, from related U.S. Appl. No. 15/003,797, 29 pages.
U.S. Office Action dated Jun. 1, 2017, from related U.S. Appl. No. 15/179,957, 29 pages.
U.S. Office Action dated Jun. 12, 2017, from related U.S. Appl. No. 15/003,256, 9 pages.
U.S. Office Action dated Jun. 12, 2017, from related U.S. Appl. No. 15/003,336, 14 pages.
U.S. Office Action dated Jun. 16, 2017, from related U.S. Appl. No. 15/003,678, 15 pages.
U.S. Office Action dated Jun. 2, 2017, from related U.S. Appl. No. 15/476,636, 10 pages.
Wroble, "Performance Analysis of Magnetic Indoor Local Positioning System." Western Michigan University Master's Theses, Paper 609 (Jun. 2015), 42 pages.
U.S. Notice of Allowance dated Oct. 19, 2017, from related U.S. Appl. No. 15/179,957, 5 pages.
U.S. Notice of Allowance dated Oct. 23, 2017, from related U.S. Appl. No. 15/003,797, 6 pages.
U.S. Office Action dated Nov. 27, 2017, from related U.S. Appl. No. 15/468,386, 28 pages.
Fallah et al., "Multi-sensor approach in vessel magnetic wake imaging," Wave Motion 51(1): 60-76 (Jan. 2014), retrieved from http://www.sciencedirect.com/science/article/pii/S0165212513001133 (Aug. 21, 2016), 17 pages.
International Preliminary Report on Patentability dated Oct. 20, 2016 from related PCT application PCT/US2015/024723, 7 pages.
International Search Report and Written Opinion of the International Searching Authority dated Sep. 13, 2016 from related PCT application PCT/US16/14377, 11 pages.
Notice of Allowance dated Aug. 17, 2016, from related U.S. Appl. No. 15/003,718, 8 pages.
Notice of Allowance dated Sep. 8, 2016, from related U.S. Appl. No. 15/003,298, 10 pages.
Soykal et al., "Quantum metrology with a single spin-3/2 defect in silicon carbide," Mesoscale and Nanoscale Physics (May 24, 2016), retrieved from https://arxiv.org/abs/1605.07628 (Sep. 22, 2016), 9 pages.
Teale, "Magnetometry with Ensembles of Nitrogen Vacancy Centers in Bulk Diamond," Master's Thesis, Massachusetts Institute of Technology Department of Electrical Engineering and Computer Science (Sep. 2015), 57 pages.
U.S. Office Action dated Aug. 24, 2016 from related U.S. Appl. No. 14/676,740, 19 pages.
U.S. Office Action dated Oct. 14, 2016 from related U.S. Appl. No. 15/003,677, 13 pages.
U.S. Office Action dated Oct. 19, 2016 from related U.S. Appl. No. 15/218,821, 6 pages.
U.S. Office Action dated Nov. 2, 2016 from related U.S. Appl. No. 15/003,256, 19 pages.
U.S. Office Action dated Nov. 3, 2016 from related U.S. Appl. No. 15/204,675, 9 pages.

(56) References Cited

OTHER PUBLICATIONS

Widmann et al., "Coherent control of single spins in silicon carbide at room temperature," Nature Materials, 14: 164-168 (Feb. 2015) (available online Dec. 1, 2014), 5 pages.
International Search Report and Written Opinion of the International Searching Authority in PCT/US2016/014390 dated Feb. 15, 2017.
Notice of Allowance dated Dec. 13, 2016, from related U.S. Appl. No. 14/680,877.
Notice of Allowance dated Dec. 22, 2016, from related U.S. Appl. No. 14/659,498.
U.S. Notice of Allowance dated Feb. 14, 2017, from related U.S. Appl. No. 15/003,677, 8 pages.
U.S. Office Action dated Feb. 10, 2017, from related U.S. Appl. No. 14/676,740, 38 pages.
U.S. Office Action dated Feb. 10, 2017, from related U.S. Appl. No. 15/003,088, 32 pages.
U.S. Office Action dated Feb. 16, 2017, from related U.S. Appl. No. 15/204,675, 15 pages.
Acosta et al., "Broadband magnetometry by infrared-absorption detection of nitrogen-vacancy ensembles in diamond," Appl. Phys. Letters 97: 174104 (Oct. 29, 2010), 4 pages.
Barry et al., "Optical magnetic detection of single-neuron action potentials using quantum defects in diamond," as submitted to Quantum Physics on Feb. 2, 2016, 23 pages.
Constable, "Geomagnetic Spectrum, Temporal." In Encyclopedia of Geomagnetism and Paleomagnetism, pp. 353-355, Springer: Dordrecht, Netherlands (2007).
International Search Report and Written Opinion of the International Searching Authority dated Apr. 1, 2016 from related PCT application PCT/US2016/014384, 12 pages.
International Search Report and Written Opinion of the International Searching Authority dated Apr. 11, 2016 from related PCT application PCT/US2016/014376, 12 pages.
International Search Report and Written Opinion of the International Searching Authority dated Apr. 11, 2016 from related PCT application PCT/US2016/014388, 14 pages.
International Search Report and Written Opinion of the International Searching Authority dated Apr. 11, 2016 from related PCT application PCT/US2016/014395, 15 pages.
International Search Report and Written Opinion of the International Searching Authority dated Jul. 6, 2015, from related PCT application PCT/US2015/021093, 9 pages.
International Search Report and Written Opinion of the International Searching Authority dated Jul. 8, 2015, from related PCT application PCT/US2015/024265, 11 pages.
International Search Report and Written Opinion of the International Searching Authority dated Jul. 12, 2016 from related PCT application PCT/US2016/014287, 14 pages.
International Search Report and Written Opinion of the International Searching Authority dated Jul. 16, 2015, from related PCT application PCT/US2015/24723, 8 pages.
International Search Report and Written Opinion of the International Searching Authority dated Jun. 10, 2016 from related PCT application PCT/US2016/014290, 11 pages.
International Search Report and Written Opinion of the International Searching Authority dated Jun. 2, 2016 from related PCT application PCT/US2016/014386, 14 pages.
International Search Report and Written Opinion of the International Searching Authority dated Jun. 2, 2016 from related PCT application PCT/US2016/014387, 13 pages.
International Search Report and Written Opinion of the International Searching Authority dated Jun. 6, 2016 from related PCT application PCT/US2016/014291, 13 pages.
International Search Report and Written Opinion of the International Searching Authority dated Jun. 9, 2016 from related PCT application PCT/US2016/014333, 16 pages.
International Search Report and Written Opinion of the International Searching Authority dated Mar. 24, 2016 from related PCT application PCT/US2016/014336, 17 pages.
International Search Report and Written Opinion of the International Searching Authority dated Mar. 24, 2016 from related PCT application PCT/US2016/014297, 15 pages.
International Search Report and Written Opinion of the International Searching Authority dated Mar. 24, 2016 from related PCT application PCT/US2016/014392, 8 pages.
International Search Report and Written Opinion of the International Searching Authority dated Mar. 24, 2016 from related PCT application PCT/US2016/014403, 10 pages.
International Search Report and Written Opinion of the International Searching Authority dated Mar. 25, 2016, from related PCT application PCT/US2016/014363, 8 pages.
International Search Report and Written Opinion of the International Searching Authority dated Mar. 25, 2016, from related PCT application PCT/US2016/014389, 19 pages.
International Search Report and Written Opinion of the International Searching Authority dated Mar. 28, 2016, from related PCT application PCT/US2016/014380, 9 pages.
International Search Report and Written Opinion of the International Searching Authority dated Mar. 28, 2016 from related PCT application PCT/US2016/014394, 17 pages.
International Search Report and Written Opinion of the International Searching Authority dated Mar. 29, 2016 from related PCT application PCT/US2016/014325, 11 pages.
International Search Report and Written Opinion of the International Searching Authority dated Mar. 29, 2016 from related PCT application PCT/US2016/014330, 8 pages.
International Search Report and Written Opinion of the International Searching Authority dated Mar. 29, 2016, from related PCT application PCT/US/2016014328, 7 pages.
International Search Report and Written Opinion of the International Searching Authority dated Mar. 29, 2016, from related PCT application PCT/US2016/014385, 11 pages.
International Search Report and Written Opinion of the International Searching Authority dated Mar. 30, 2016 from related PCT application PCT/US2016/014298, 14 pages.
International Search Report and Written Opinion of the International Searching Authority dated Mar. 31, 2016 from related PCT application PCT/US2016/014375, 11 pages.
International Search Report and Written Opinion of the International Searching Authority dated Mar. 31, 2016 from related PCT application PCT/US2016/014396, 11 pages.
International Search Report and Written Opinion of the International Searching Authority dated May 26, 2016, 2016 from related PCT application PCT/US2016/014331, 15 pages.
Le Sage et al., "Efficient photon detection from color centers in a diamond optical waveguide," Phys. Rev. B 85: 121202(R), pp. 121202-1-121202-4, (Mar. 23, 2012).
Macquarie et al., "Mechanical spin control of nitrogen-vacancy centers in diamond," Retrieved from http://www.arxiv.org/pdf/1306.6356.pdf, pp. 1-8, (Jun. 2013).
Nobauer et al., "Smooth optimal quantum control for robust solid state spin magnetometry," Retrieved from http://www.arxiv.org/abs/1412.5051, pp. 1-12, (Dec. 2014).
Polatomic. "AN/ASQ-233A Digital Magnetic Anomaly Detecting Set." Retrieved May 9, 2016, from http://polatomic.com/images/DMAD_Data_Sheet_09-2009.pdf (2009), 1 page.
Poole, "What is GMSK Modulation—Gaussian Minimum Shift Keying." Radio-Electronics, retrieved from https://web.archive.org/web/20150403045840/http://www.radio-electronics.com/info/rf-technology-design/pm-phase-modulation/what-is-gmsk-gaussian-minimum-shift-keyingtutorial.php (Apr. 3, 2015), 4 pages.
Shao et al., "Diamond Color Center Based FM Microwave Demodulator," in Conference on Lasers and Electro-Optics, OSA Technical Digest (online) (Optical Society of America), paper JTh2A.136, 2 pages. (Jun. 5-10, 2016).
U.S. Notice of Allowance dated Apr. 20, 2016, from related U.S. Appl. No. 15/003,718, 9 pages.
U.S. Notice of Allowance dated Mar. 29, 2016, from related U.S. Appl. No. 15/003,590, 11 pages.
U.S. Office Action dated Jul. 29, 2016 from related U.S. Appl. No. 14/680,877, 8 pages.

(56) References Cited

OTHER PUBLICATIONS

U.S. Office Action dated May 13, 2016, from related U.S. Appl. No. 14/676,740, 15 pages.
U.S. Office Action dated May 6, 2016, from related U.S. Appl. No. 14/659,498, 20 pages.
Wahlstrom et al., "Modeling Magnetic Fields Using Gaussian Processes," 2013 IEEE International Conference on Acoustics, Speech, and Signal Processing, pp. 3522-3526 (May 26-31, 2013).
U.S. Appl. No. 14/866,730, filed Sep. 25, 2015.
U.S. Appl. No. 15/179,957, filed Jun. 10, 2016.
U.S. Appl. No. 15/207,457, filed Jul. 11, 2016.
U.S. Appl. No. 15/218,821, filed Jul. 25, 2016.
U.S. Appl. No. 15/204,675, filed Jul. 7, 2016.
U.S. Appl. No. 15/446,373, filed Mar. 1, 2017.
U.S. Appl. No. 15/450,504, filed Mar. 6, 2017.
U.S. Appl. No. 15/454,162, filed Mar. 9, 2017.
U.S. Appl. No. 15/456,913, filed Mar. 13, 2017.
U.S. Appl. No. 15/468,356, filed Mar. 24, 2017.
U.S. Appl. No. 15/468,397, filed Mar. 24, 2017.
U.S. Appl. No. 15/468,386, filed Mar. 24, 2017.
U.S. Appl. No. 15/468,289, filed Mar. 24, 2017.
U.S. Appl. No. 15/468,641, filed Mar. 24, 2017.
U.S. Appl. No. 15/468,582, filed Mar. 24, 2017.
U.S. Appl. No. 15/468,410, filed Mar. 24, 2017.
U.S. Appl. No. 15/468,951, filed Mar. 24, 2017.
U.S. Appl. No. 15/468,559, filed Mar. 24, 2017.
U.S. Appl. No. 15/468,282, filed Mar. 24, 2017.
U.S. Appl. No. 15/468,314, filed Mar. 24, 2017.
U.S. Appl. No. 15/468,274, filed Mar. 24, 2017.
U.S. Appl. No. 15/468,303, filed Mar. 24, 2017.
U.S. Appl. No. 15/469,374, filed Mar. 24, 2017.
U.S. Appl. No. 15/476,636, filed Mar. 31, 2017.
U.S. Appl. No. 15/479,256, filed Apr. 4, 2017.
U.S. Appl. No. 15/003,145, filed Jan. 21, 2016.
U.S. Appl. No. 15/350,303, filed Nov. 14, 2016.
U.S. Appl. No. 15/351,862, filed Jul. 7, 2016.
U.S. Appl. No. 15/372,201, filed Dec. 7, 2016.
U.S. Appl. No. 15/376,244, filed Dec. 12, 2016.
U.S. Appl. No. 15/380,691, filed Dec. 15, 2016.
U.S. Appl. No. 15/382,045, filed Dec. 16, 2016.
U.S. Appl. No. 15/380,419, filed Dec. 15, 2016.
U.S. Appl. No. 15/419,832, filed Jan. 30, 2017.
U.S. Appl. No. 15/400,794, filed Jan. 6, 2017.
U.S. Appl. No. 15/443,422, filed Jan. 27, 2017.
U.S. Appl. No. 15/440,194, filed Feb. 23, 2017.
U.S. Appl. No. 15/437,222, filed Feb. 20, 2017.
U.S. Appl. No. 15/437,038, filed Feb. 20, 2017.
GB Office Action dated Jan. 10, 2017, in related national stage application GB1618202.4.
"Diamond Sensors, Detectors, and Quantum Devices' in Patent Application Approval Process," Chemicals & Chemistry (Feb. 28, 2014).
"Findings from University of Stuttgart in physics reported," Physics Week (Jul. 7, 2009).
"New Findings on Nitrogen from Ecole Normale Superieure Summarized (Magnetic imaging with an ensemble of nitrogen vacancy-centers in diamond)," Physics Week (Jul. 21, 2015).
"Patent Issued for Diamond Sensors, Detectors, and Quantum Devices (U.S. Pat. No. 9,249,526)," Journal of Engineering (Feb. 15, 2016).
"Researchers Submit Patent Application, 'Diamond Sensors, Detectors, and Quantum Devices', for Approval," Chemicals & Chemistry (Apr. 11, 2014).
Acosta, "Optical Magnetometry with Nitrogen-Vacancy Centers in Diamond," University of California Berkeley, 2011.
Acosta, et al., "Diamonds with a high density of nitrogen—vacancy centers for magnetometry applications," Physical Review B, Sep. 2009.
Acosta, et al., "Nitrogen-vacancy centers: physics and applications," MRS Bulletin, 2013.

Aiello, et al., "Composite-pulse magnetometry with a solid-state quantum sensor," Nature Communications, Jan. 2013.
Alam, "Solid-state C-13 magic angle spinning NMR spectroscopy characterization of particle size structural variations in synthetic nanodiamonds," Materials Chemistry and Physics, Jun. 2004.
Albrecht, et al., "Coupling of nitrogen vacancy centres in nanodiamonds by means of phonons," New Journal of Physics, Aug. 2013.
Anthony, et al., "Jahn-Teller Splitting and Zeeman Effect of Acceptors in Diamond," 20th International Conference on Defects in Semiconductors, Jul. 1999.
Appel, et al., "Nanoscale microwave imaging with a single electron spin in diamond," New Journal of Physics, Nov. 2015.
Arai, et al., "Fourier magnetic imaging with nanoscale resolution and compressed sensing speed-up using electronic spins in diamond," Nature Nanotechnology, Oct. 2015.
Aslam, et al., "Single spin optically detected magnetic resonance with 60-90 GHz (E-band) microwave resonators," Review of Scientific Instruments, Jun. 2015.
Awschalom, et al., "Diamond age of spintronics," Scientific American, Oct. 2007.
Babamoradi, et al., "Correlation between entanglement and spin density in nitrogen-vacancy center of diamond," European Physical Journal D, Dec. 2011.
Babunts, et al., "Diagnostics of NV defect structure orientation in diamond using optically detected magnetic resonance with a modulated magnetic field," Technical Physics Letters, Jun. 2015.
Babunts, et al., "Temperature-scanned magnetic resonance and the evidence of two-way transfer of a nitrogen nuclear spin hyperfine interaction in coupled NV-N pairs in diamond," JETP Letters, Jun. 2012.
Bagguley, et al., "Zeeman effect of acceptor states in semiconducting diamond," Journal of the Physical Society of Japan, 1966.
Balasubramanian, et al., "Nanoscale imaging magnetometry with diamond spins under ambient conditions," Nature, Oct. 2008.
Balmer, et al., "Chemical Vapour deposition synthetic diamond: materials technology and applications," J. of Physics, 2009.
Baranov, et al., "Enormously High Concentrations of Fluorescent Nitrogen-Vacancy Centers Fabricated by Sintering of Detonation Nanodiamonds," Small, Jun. 2011.
Barfuss, et al., "Strong mechanical driving of a single electron spin," Nature Physics, Oct. 2015.
Bennett, et al., "CVD Diamond for High Power Laser Applications," Proceedings of SPIE, Jan. 2013.
Berman & Chernobrod, "Single-spin microscope with sub-nanoscale resolution based on optically detected magnetic resonance," Proceedings of SPIE, May 2010.
Berman, et al. "Measurement of single electron and nuclear spin states based on optically detected magnetic resonance," J. Physics: Conf. Series 38: 167-170 (2006).
Blakley, et al., "Room-temperature magnetic gradiometry with fiber-coupled nitrogen—vacancy centers in diamond," Optics Letters, Aug. 2015.
Bourgeois, et al., "Photoelectric detection of electron spin resonance of nitrogen-vacancy centres in diamond," Nature Communications, Oct. 2015.
Budker & Kimball, "Optical Magnetometry," Cambridge Press, 2013.
Budker & Romalis, "Optical Magnetometry," Nature Physics, 2007.
Casanova, et al., "Effect of magnetic field on phosphorus centre in diamond," Physica Status Solidi A, Jul. 2001.
Castelletto, et al., "Frontiers in diffraction unlimited optical methods for spin manipulation, magnetic field sensing and imaging using diamond nitrogen vacancy defects," Nanophotonics, 2012.
Chapman, et al., "Anomalous saturation effects due to optical spin depolarization in nitrogen-vacancy centers in diamond nanocrystals," Physical Review B, Jul. 2012.
Chen, et al., "Vector magnetic field sensing by a single nitrogen vacancy center in diamond," EPL, Mar. 2013.
Chernobrod, et al., "Improving the sensitivity of frequency modulation spectroscopy using nanomechanical cantilevers," Applied Physics Letters, 2004.
Chernobrod, et al., "Spin Microscope Based on Optically Detected Magnetic Resonance," Journal of Applied Physics, 2005.

(56) References Cited

OTHER PUBLICATIONS

Childress, et al., "Coherent dynamics of coupled electron and nuclear spin qubits in diamond," Science, 2006.
Chipaux, et al., "Magnetic imaging with an ensemble of nitrogen vacancy-centers in diamond," European Physical Journal D, Jul. 2015.
Chipaux, et al., "Nitrogen vacancies (NV) centers in diamond for magnetic sensors and quantum sensing," Proceedings of SPIE, Jan. 2015.
Chipaux, et al., "Wide bandwidth instantaneous radio frequency spectrum analyzer based on nitrogen vacancy centers in diamond," Applied Physics Letters, Dec. 2015.
Clevenson, et al., "Broadband magnetometry and temperature sensing with a light-trapping diamond waveguide," Nature Physics, May 2015.
Cooper, et al., "Time-resolved magnetic sensing with electronic spins in diamond," Nature Communications, Jan. 2014.
Creedon, et al., "Strong coupling between P1 diamond impurity centers and a three-dimensional lumped photonic microwave cavity," Physical Review B, Apr. 2015.
Davies, "Current problems in diamond: towards a quantitative understanding," Physica B—Condensed Matter, Dec. 1999.
De Lange, et al., "Single-Spin Magnetometry with Multipulse Sensing Sequences," Physical Review Letters, Feb. 2011.
Degen, "Scanning magnetic field microscope with a diamond single-spin sensor," Applied Physics Letters, 2008.
Delacroix, et al., "Design, manufacturing, and performance analysis of mid-infrared achromatic half-wave plates with diamond subwavelength gratings," Applied Optics, 2012.
Denatale, et al., "Fabrication and characterization of diamond moth eye antireflective surfaces on Ge," J. of Applied Physics, 1982.
Dobrovitski, et al., "Quantum Control over Single Spins in Diamond," Annual Review of Condensed Matter Physics vol. 4, 2013.
Doherty, et al., "The nitrogen-vacancy colour centre in diamond," Physics Reports, Jul. 2013.
Doherty, et al., "Theory of the ground-state spin of the NV-center in diamond," Physical Review B, May 2012.
Doi, et al., "Pure negatively charged state of the NV center in n-type diamond," Physical Review B, Feb. 2016.
Drake, et al., "Influence of magnetic field alignment and defect concentration on nitrogen-vacancy polarization in diamond," New Journal of Physics, Jan. 2016.
Dreau, et al., "Avoiding power broadening in optically detected magnetic resonance of single NV defects for enhanced dc magnetic field sensitivity," Physical Review B, Nov. 2011.
Dreau, et al., "High-resolution spectroscopy of single NV defects coupled with nearby C-13 nuclear spins in diamond," Physical Review B, Apr. 2012.
Dumeige, et al., "Magnetometry with nitrogen—vacancy ensembles in diamond based on infrared absorption in a doubly resonant optical cavity," Physical Review B, Apr. 2013.
Epstein, et al., "Anisotropic interactions of a single spin and dark-spin spectroscopy in diamond," Center for Spintronics and Quantum Computation, 2005.
Fedotov, et al., "High-resolution magnetic field imaging with a nitrogen-vacancy diamond sensor integrated with a photonic-crystal fiber," Optics Letters, Feb. 2016.
Fedotov, et al., "Photonic-crystal-fiber-coupled photoluminescence interrogation of nitrogen vacancies in diamond nanoparticles," Laser Physics Letters, Feb. 2012.
Feng & Wei, "A steady-state spectral method to fit microwave absorptions of NV centers in diamonds: application to sensitive magnetic field sensing," Measurement Science & Technology, Oct. 2014.
Freitas, et al., "Solid-State Nuclear Magnetic Resonance (NMR) Methods Applied to the Study of Carbon Materials," Chemistry and Physics of Carbon, vol. 31, 2012.
Geiselmann, et al., "Fast optical modulation of the fluorescence from a single nitrogen-vacancy centre," Nature Physics, Dec. 2013.

Gombert & Blasi, "The Moth-Eye Effect—From Fundamentals to Commercial Exploitation," Functional Properties of Bio-Inspired Surfaces, Nov. 2009.
Gong, et al., "Generation of Nitrogen-Vacancy Center Pairs in Bulk Diamond by Molecular Nitrogen Implantation," Chinese Physics Letters, Feb. 2016.
Gould, et al., "An imaging magnetometer for bio-sensing based on nitrogen-vacancy centers in diamond," Proceedings of the SPIE—Progress in Biomedical Optics and Imaging, 2014.
Gould, et al., "Room-temperature detection of a single 19 nm super-paramagnetic nanoparticle with an imaging magnetometer," Applied Physics Letters, Aug. 2014.
Gruber, et al., "Scanning confocal optical microscopy and magnetic resonance on single defect centers," Science, Jun. 1997.
Haeberle, et al., "Nanoscale nuclear magnetic imaging with chemical contrast," Nature Nanotechnology, Feb. 2015.
Haihua, et al., "Design of wideband anti-reflective sub wavelength nanostructures," Infrared and Laser Engineering, 2011.
Hall, et al., "Sensing of Fluctuating Nanoscale Magnetic Fields Using Nitrogen—Vacancy Centers in Diamond," Physical Review Letters, Nov. 2009.
Hanson, et al., "Coherent Dynamics of a single spin interacting with an adjustable spin bath," Sci. Am. Ass'n for the Advancement of Science, 2008.
Hanson, et al., "Polarization and Readout of Coupled Single Spins in Diamond," Physical Review Letters, 2006.
Hanson, et al., "Room-temperature manipulation and decoherence of a single spin in diamond," Physical Review, 2006.
Hanzawa, et al., "Zeeman effect on the zero-phonon line of the NV center in synthetic diamond," Physica B, Feb. 1993.
Hegyi & Yablonovitch, "Molecular imaging by optically detected electron spin resonance of nitrogen-vacancies in nanodiamonds," Nano Letters, Mar. 2013.
Hegyi & Yablonovitch, "Nanodiamond molecular imaging with enhanced contrast and expanded field of view," Journal of Biomedical Optics, Jan. 2014.
Hilser, et al., "All-optical control of the spin state in the NV-center in diamond," Physical Review B, Sep. 2012.
Hobbs, "Study of the Environmental and Optical Durability of AR Microstructures in Sapphire, ALON, and Diamond," Proceedings of SPIE, 2009.
Huebener, et al., "ODMR of NV centers in nano-diamonds covered with N@C60," Physica Status Solidi B, Oct. 2008.
Huxter, et al., "Vibrational and electronic dynamics of nitrogen-vacancy centres in diamond revealed by two-dimensional ultrafast spectroscopy," Nature Physics, Nov. 2013.
Ivady, et al., "Pressure and temperature dependence of the zero-field splitting in the ground state of NV centers in diamond: A first-principles study," Physical Review B, Dec. 2014.
Jarmola, et al., "Temperature- and Magnetic-Field-Dependent Longitudinal Spin Relaxation in Nitrogen-Vacancy Ensembles in Diamond," Physical Review Letters, May 2012.
Jensen, et al., "Light narrowing of magnetic resonances in ensembles of nitrogen-vacancy centers in diamond," Physical Review, Jan. 2013.
Kailath, "Linear Systems," Prentice Hall, 1979.
Karlsson, et al., "Diamond micro-optics: microlenses and antireflection structures surfaces for the infrared spectral region," Optics Express, 2003.
Khan & Hemmer, "Noise limitation in nano-scale imaging," Proceedings of SPIE, Dec. 2005.
Kim, et al., "Electron spin resonance shift and linewidth broadening of nitrogen-vacancy centers in diamond as a function of electron irradiation dose," Applied Physics Letters, Aug. 2012.
Kim, et al., "Magnetospectroscopy of acceptors in 'blue' diamonds," Physica B, Aug. 2001.
Kim, et al., "Zeeman effect of electronic Raman lines of accepters in elemental semiconductors: Boron in blue diamond," Physical Review B, Sep. 2000.
King, et al., "Optical polarization of 13C nuclei in diamond through nitrogen vacancy centers," Physical Review B, Feb. 2010.
Kok, et al., "Materials Science: Qubits in the pink," Nature, 2006.

(56) References Cited

OTHER PUBLICATIONS

Konenko, et al., "Formation of antireflective surface structures on diamond films by laser patterning," Applied Physics A, 1999.
Kraus, et al., "Magnetic field and temperature sensing with atomic-scale spin defects in silicon carbide," Scientific Reports, Jul. 2014.
Lai, et al., "Influence of a static magnetic field on the photoluminescence of an ensemble of nitrogen-vacancy color centers in a diamond single-crystal," Applied Physics Letters, Sep. 2009.
Lai, et al., "Optically detected magnetic resonance of a single Nitrogen-Vacancy electronic spin in diamond nanocrystals," CLEO/EQEC, 2009.
Laraoui, et al., "Nitrogen-vacancy-assisted magnetometry of paramagnetic centers in an individual diamond nanocrystal," Nano Letters, Jul. 2012.
Lazariev, et al., "A nitrogen-vacancy spin based molecular structure microscope using multiplexed projection reconstruction," Scientific Reports, Sep. 2015.
Lee, et al., "Vector magnetometry based on S=3/2 electronic spins," Physical Review B, Sep. 2015.
Lesik, et al., "Preferential orientation of NV defects in CVD diamond films grown on (113)-oriented substrates," Diamond and Related Materials, Jun. 2015.
Levchenko, et al., "Inhomogeneous broadening of optically detected magnetic resonance of the ensembles of nitrogen-vacancy centers in diamond by interstitial carbon atoms," Applied Physics Letters, Mar. 2015.
Liu, et al., "Electron spin studies of nitrogen vacancy centers in nanodiamonds," Acta Physica Sinica, Aug. 2013.
Liu, et al., "Fiber-integrated diamond-based magnetometer," Applied Physics Letters, Sep. 2013.
MacLaurin, et al., "Nanoscale magnetometry through quantum control of nitrogen-vacancy centres in rotationally diffusing nanodiamonds," New Journal of Physics, Jan. 2013.
Macs, et al., "Diamond as a magnetic field calibration probe," Journal of Physics D: Applied Physics, Apr. 2004.
Maletinsky, et al., "A robust scanning diamond sensor for nanoscale imaging with single nitrogen-vacancy centres," Nature Nanotechnology, May 2012.
Mamin, et al., "Multipulse Double-Quantum Magnetometry with Near-Surface Nitrogen-Vacancy Centers," Physical Review Letters, Jul. 2014.
Mamin, et al., "Nanoscale Nuclear Magnetic Resonance with a Nitrogen-Vacancy Spin Sensor," Science, Feb. 2013.
Manson, et al., "GR transitions in diamond: magnetic field measurements," Journal of Physics C, Nov. 1980.
Massachusetts Institute of Technology; "Wide-Field Imaging Using Nitrogen Vacancies" in Patent Application Approval Process, Physics Week (2015).
Matsuda, et al., "Development of a plastic diamond anvil cell for high pressure magneto-photoluminescence in pulsed high magnetic fields," International Journal of Modern Physics B, Nov. 2004.
Maze et al., "Nanoscale magnetic sensing with an individual electronic spin in diamond," Nature Physics (2008).
Maze, et al., "Nanoscale magnetic sensing using spin qubits in diamond," Nature Physics, 2009.
Meijer, et al., "Generation of single color centers by focused nitrogen implantation," Applied Physics Letters, Dec. 2005.
Millot, et al., "High-field Zeeman and paschen-back effects at high pressure in oriented ruby," Physical Review B, Oct. 2008.
Moriyama, et al., "Importance of electron-electron interactions and Zeeman splitting in single-wall carbon nanotube quantum dots," Physica E, Feb. 2005.
Mrozek, et al., "Circularly polarized microwaves for magnetic resonance study in the GHz range: Application to nitrogen-vacancy in diamonds," Applied Physics Letters, Jul. 2015.
Nagl, et al., "Improving surface and defect center chemistry of fluorescent nanodiamonds for imaging purposes—a review," Analytical and Bioanalaytical Chemistry, Oct. 2015.

Neumann, et al., "Excited-state spectroscopy of single NV defects in diamond using optically detected magnetic resonance," New Journal of Physics, Jan. 2009.
Nizovtsev & Kilin, "Optically Detected Magnetic Resonance Spectra of the 14NV-13C Spin Systems in Diamond: Analytical Theory and Experiment," Doklady of the National Academy of Sciences of Belarus, 2013.
Nizovtsev, et al., "Modeling fluorescence of single nitrogen-vacancy defect centers in diamond," Physica B—Condensed Matter, Dec. 2001.
Nizovtsev, et al., "Theoretical study of hyperfine interactions and optically detected magnetic resonance spectra by simulation of the C-291(NV)H—(172) diamond cluster hosting nitrogen-vacancy center," New Journal of Physics, Aug. 2014.
Nowodzinski, et al., "Nitrogen-Vacancy centers in diamond for current imaging at the redistributive layer level of Integrated Circuits," Microelectronics Reliability, Aug. 2015.
Nusran, et al., "Optimizing phase-estimation algorithms for diamond spin magnetometry," Physical Review B, Jul. 2014.
Ohashi, et al., "Negatively Charged Nitrogen-Vacancy Centers in a 5 nm Thin C-12 Diamond Film," Nano Letters, Oct. 2013.
Plakhotnik, et al., "Super-Paramagnetic Particles Chemically Bound to Luminescent Diamond : Single Nanocrystals Probed with Optically Detected Magnetic Resonance," Journal of Physical Chemistry C, Aug. 2015.
Rabeau, et al., "Implantation of labelled single nitrogen vacancy centers in diamond using N-15," Applied Physics Letters, Jan. 2006.
Ranjbar, et al., "Many-electron states of nitrogen-vacancy centers in diamond and spin density calculations," Physical Review B, Oct. 2011.
Reynhardt, "Spin-lattice relaxation of spin-½ nuclei in solids containing diluted paramagnetic impurity centers. I. Zeeman polarization of nuclear spin system," Concepts in Magnetic Resonance Part A, Sep. 2003.
Rogers, et al., "Singlet levels of the NV(-) centre in diamond," New Journal of Physics, Jan. 2015.
Rondin, et al., "Magnetometry with nitrogen-vacancy defects in diamond," Reports on Progress in Physics, May 2014.
Rondin, et al., "Nanoscale magnetic field mapping with a single spin scanning probe magnetometer," Applied Physics Letters, Apr. 2012.
Sarkar, et al., "Magnetic properties of graphite oxide and reduced graphene oxide," Physica E, 2014.
Scheuer, et al., "Accelerated 2D magnetic resonance spectroscopy of single spins using matrix completion," Scientific Reports, Dec. 2015.
Schirhagl, et al., "Nitrogen-vacancy centers in diamond: Nanoscale sensors for physics and biology," Annual Review of Physical Chemistry, Jan. 2014.
Schoenfeld & Harneit, "Real time magnetic field sensing and imaging using a single spin in diamond," Physical Review Letters, Jan. 2011.
Sedov, et al., "Si-doped nano- and microcrystalline diamond films with controlled bright photoluminescence of silicon-vacancy color centers," Diamond and Related Materials, Jun. 2015.
Shames, et al., "Magnetic resonance tracking of fluorescent nanodiamond fabrication," Journal of Physics D: Applied Physics, Apr. 2015.
Simanovskaia, et al., "Sidebands in optically detected magnetic resonance signals of nitrogen vacancy centers in diamond," Physical Review B, Jun. 2013.
Sotoma, et al., "Effective production of fluorescent nanodiamonds containing negatively-charged nitrogen-vacancy centers by ion irradiation," Diamond and Related Materials, Oct. 2014.
Steiner, et al., "Universal enhancement of the optical readout fidelity of single electron spins at nitrogen-vacancy centers in diamond," Physical Review B, Jan. 2010.
Steinert et al., "High-sensitivity magnetic imaging using an array of spins in diamond," Rev. Sci. Inst. (2010).
Steinert, et al., "High sensitivity magnetic imaging using an array of spins in diamond," Review of Scientific Instruments, Apr. 2010.
Stepanov, et al., "High-frequency and high-field optically detected magnetic resonance of nitrogen-vacancy centers in diamond," Applied Physics Letters, Feb. 2015.

(56) References Cited

OTHER PUBLICATIONS

Sternschulte, et al., "Uniaxial stress and Zeeman splitting of the 1.681 eV optical center in a homoepitaxial CVD diamond film," Diamond and Related Materials, Sep. 1995.
Storteboom, et al., "Lifetime investigation of single nitrogen vacancy centres in nanodiamonds," Optics Express, May 2015.
Tahara, et al., "Quantifying selective alignment of ensemble nitrogen-vacancy centers in (111) diamond," Applied Physics Letters, Nov. 2015.
Taylor, et al., "High-sensitivity diamond magnetometer with nanoscale resolution," Nature Physics, Oct. 2008.
Terblanche, et al., "13C spin-lattice relaxation in natural diamond: Zeeman relaxation at 4.7 T and 300 K due to fixed paramagnetic nitrogen defects," Solid State Nuclear Magnetic Resonance, Aug. 2001.
Terblanche, et al., "13C spin-lattice relaxation in natural diamond: Zeeman relaxation in fields of 500 to 5000 G at 300 K due to fixed paramagnetic nitrogen defects," Solid State Nuclear Magnetic Resonance, May 2001.
Tetienne, et al., "Magnetic-field-dependent photodynamics of single NV defects in diamond: an application to qualitative all-optical magnetic imaging," New Journal of Physics, Oct. 2012.
Tong, et al., "A hybrid-system approach for W state and cluster state generation," Optics Communication 310: 166-172 (2014).
Uhlen, et al., "New Diamond Nanofabrication process for hard x-ray zone plates," J. of Vacuum Science & Tech. B, 2011.
Vershovskii & Dmitriev, "Combined excitation of an optically detected magnetic resonance in nitrogen-vacancy centers in diamond for precision measurement of the components of a magnetic field vector," Technical Physics Letters, Nov. 2015.
Vershovskii & Dmitriev, "Micro-scale three-component quantum magnetometer based on nitrogen-vacancy color centers in diamond crystal," Technical Physics Letters, Apr. 2015.
Wang, et al., "Optimizing ultrasensitive single electron magnetometer based on nitrogen-vacancy center in diamond," Chinese Science Bulletin, Aug. 2013.
Webber, et al., "Ab initio thermodynamics calculation of the relative concentration of NV- and NV0 defects in diamond," Physical Review B, Jan. 2012.
Wolf, et al., "Subpicotesla Diamond Magnetometry," Physical Review X, Oct. 2015.
Wolfe, et al., "Off-resonant manipulation of spins in diamond via precessing magnetization of a proximal ferromagnet," Physical Review B, May 2014.
Xue & Liu, "Producing GHZ state of nitrogen-vacancy centers in cavity QED," Journal of Modern Optics, Mar. 2013.
Yang & Gu, "Novel calibration techniques for high pulsed-magnetic fields using luminescence caused by photo," (with English machine translation), Journal of Huazhong University of Science and Technology, Jun. 2007.
Yavkin, et al., "Defects in Nanodiamonds: Application of High-Frequency cw and Pulse EPR, ODMR," Applied Magnetic Resonance, Oct. 2014.
Yu, et al., "Bright fluorescent nanodiamonds: no photobleaching and low cytotoxicity," J. Am. Chem. Soc., 2005.
Zhang, et al., "Laser-polarization-dependent and magnetically controlled optical bistability in diamond nitrogen-vacancy centers," Physics Letters A, Nov. 2013.
Zhang, et al., "Laser-polarization-dependent spontaneous emission of the zero phonon line from single nitrogen-vacancy center in diamond," Chinese Physics B, Apr. 2014.
Zhang, et al., "Scalable quantum information transfer between nitrogen-vacancy-center ensembles," Annals of Physics, Apr. 2015.
Zhao, et al., "Atomic-scale magnetometry of distant nuclear spin clusters via nitrogen-vacancy spin in diamond," Nature Nanotechnology, Apr. 2011.
Bui et al., "Noninvasive Fault Monitoring of Electrical Machines by Solving the Steady-State Magnetic Inverse Problem," in IEEE Transactions on Magnetics, vol. 44, No. 6, pp. 1050-1053, Jun. 24, 2008.
Chadebec et al., "Rotor fault detection of electrical machines by low frequency magnetic stray field analysis," 2005 5th IEEE International Symposium on Diagnostics for Electric Machines, Power Electronics and Drives, Vienna, 2005, submitted Mar. 22, 2006, pp. 1-6.
Froidurot et al., "Magnetic discretion of naval propulsion machines," in IEEE Transactions on Magnetics, vol. 38, No. 2, pp. 1185-1188, Mar. 2002.
IEEE Std 802.11 TM-2012 Wireless LAN Medium Access Control (MAC) and Physical Layer (PHY) Specifications, 1 page.
Kwon et al., "Analysis of the far field of permanent-magnet motors and effects of geometric asymmetries and unbalance in magnet design," in IEEE Transactions on Magnetics, vol. 40, No. 2, pp. 435-442, Mar. 2004.
Maertz et al., "Vector magnetic field microscopy using nitrogen vacancy centers in diamond", Applied Physics Letters 96, No. 9, Mar. 1, 2010, pp. 092504-1-092504-3.
U.S. Notice of Allowance dated Feb. 2, 2018, from related U.S. Appl. No. 15/003,292, 8 pages.
U.S. Notice of Allowance dated Feb. 21, 2018, from related U.S. Appl. No. 15/003,176, 9 pages.
U.S. Office Action dated Feb. 1, 2018, from related U.S. Appl. No. 15/003,577, 16 pages.
U.S. Office Action dated Feb. 5, 2018, from related U.S. Appl. No. 15/450,504, 12 pages.
U.S. Office Action dated Jan. 25, 2018, from related U.S. Appl. No. 15/672,953, 28 pages.
U.S. Office Action dated Jan. 26, 2018, from related U.S. Appl. No. 15/003,678, 14 pages.
U.S. Office Action dated Mar. 27, 2018, from related U.S. Appl. No. 15/468,386, 21 pages.
U.S. Office Action dated Mar. 28, 2018, from related U.S. Appl. No. 15/003,177, 12 pages.
U.S. Office Action dated Mar. 5, 2018, from related U.S. Appl. No. 14/866,730, 14 pages.
U.S. Office Action dated Mar. 8, 2018, from related U.S. Appl. No. 15/380,691, 12 pages.
U.S. Office Action dated Mar. 8, 2018, from related U.S. Appl. No. 15/479,256, 30 pages.
Wegerich, "Similarity based modeling of time synchronous averaged vibration signals for machinery health monitoring," 2004 IEEE Aerospace Conference Proceedings (IEEE Cat. No. 04TH8720), 2004, pp. 3654-3662 vol. 6.
Wikipedia, "Continuous phase modulation", downloaded from https://web.archive.org/web/20151017015236/https://en.wikipedia.org/wiki/Continuous_phase_modulati on on May 10, 2017, 3 pages.
Wikipedia, "Minimum-shift keying", downloaded from https://web.archive.org/web/20151017175828/https://en.wikipedia.org/wiki/Minimum-shift_keying on May 10, 2017, 2 pages.
U.S. Appl. No. 14/659,498, filed Mar. 16, 2015.
U.S. Appl. No. 14/676,740, filed Apr. 1, 2015.
U.S. Appl. No. 14/680,877, filed Apr. 7, 2015.
U.S. Appl. No. 15/003,678, filed Jan. 21, 2016.
U.S. Appl. No. 14/866,730, filed Sep. 25, 2016.
U.S. Appl. No. 15/003,281, filed Jan. 21, 2016.
U.S. Appl. No. 15/003,292, filed Jan. 21, 2016.
U.S. Appl. No. 15/003,298, filed Jan. 21, 2016.
U.S. Appl. No. 15/003,309, filed Jan. 21, 2016.
U.S. Appl. No. 15/003,176, filed Jan. 21, 2016.
U.S. Appl. No. 15/003,336, filed Jan. 21, 2016.
U.S. Appl. No. 15/003,558, filed Jan. 21, 2016.
U.S. Appl. No. 15/003,519, filed Jan. 21, 2016.
U.S. Appl. No. 15/003,677, filed Jan. 21, 2016.
U.S. Appl. No. 15/003,256, filed Jan. 21, 2016.
U.S. Appl. No. 15/003,577, filed Jan. 21, 2016.
U.S. Appl. No. 15/003,704, filed Jan. 21, 2016.
U.S. Appl. No. 15/003,718, filed Jan. 21, 2016.
U.S. Appl. No. 15/003,062, filed Jan. 21, 2016.
U.S. Appl. No. 15/003,652, filed Jan. 21, 2016.
U.S. Appl. No. 15/003,634, filed Jan. 21, 2016.
U.S. Appl. No. 15/003,670, filed Jan. 21, 2016.
U.S. Appl. No. 15/003,088, filed Jan. 21, 2016.
U.S. Appl. No. 15/003,797, filed Jan. 21, 2016.

(56) References Cited

OTHER PUBLICATIONS

U.S. Appl. No. 15/003,590, filed Jan. 21, 2016.
U.S. Appl. No. 15/003,206, filed Jan. 21, 2016.
U.S. Appl. No. 15/003,193, filed Jan. 21, 2016.
U.S. Appl. No. 15/003,617, filed Jan. 21, 2016.
U.S. Appl. No. 15/003,396, filed Jan. 21, 2016.
U.S. Appl. No. 15/003,177, filed Jan. 21, 2016.
U.S. Appl. No. 15/003,209, filed Jan. 21, 2016.
U.S. Appl. No. 15/610,526, filed May 31, 2017.
U.S. Appl. No. 15/672,953, filed Aug. 9, 2017.
Teeling-Smith et al., "Electron Paramagnetic Resonance of a Single NV Nanodiamond Attached to an Individual Biomolecule", Biophysical Journal 110, May 10, 2016, pp. 2044-2052.
UK Office Action dated Jun. 8, 2018, from related application No. GB1617438.5, 3 pages.
US Final Office Action dated Jul. 26, 2018 from related U.S. Appl. No. 15/003,177, 14 pages.
US Non-Final Office Action dated Aug. 6, 2018 from related U.S. Appl. No. 15/376,244, 28 pages.
US Non-Final Office Action dated Aug. 9, 2018 from related U.S. Appl. No. 15/003,309, 22 pages.
US Non-Final Office Action dated Jul. 20, 2018 from related U.S. Appl. No. 15/350,303, 13 pages.
US Non-Final Office Action dated Jul. 26, 2018 from related U.S. Appl. No. 15/380,419, 11 pages.
US Non-Final Office Action dated Jul. 3, 2018 from related U.S. Appl. No. 15/003,396, 19 pages.
US Notice of Allowance dated Jul. 18, 2018 from related U.S. Appl. No. 15/468,386, 12 pages.
US Notice of Allowance dated Jul. 6, 2018 from related U.S. Appl. No. 15/672,953, 11 pages.
US Notice of Allowance dated Jun. 27, 2018 from related U.S. Appl. No. 15/003,519, 21 pages.
US Notice of Allowance dated May 15, 2018, from related U.S. Appl. No. 15/003,209, 7 pages.
US Office Action dated Jun. 19, 2018, from related U.S. Appl. No. 15/450,504, 12 pages.

\* cited by examiner

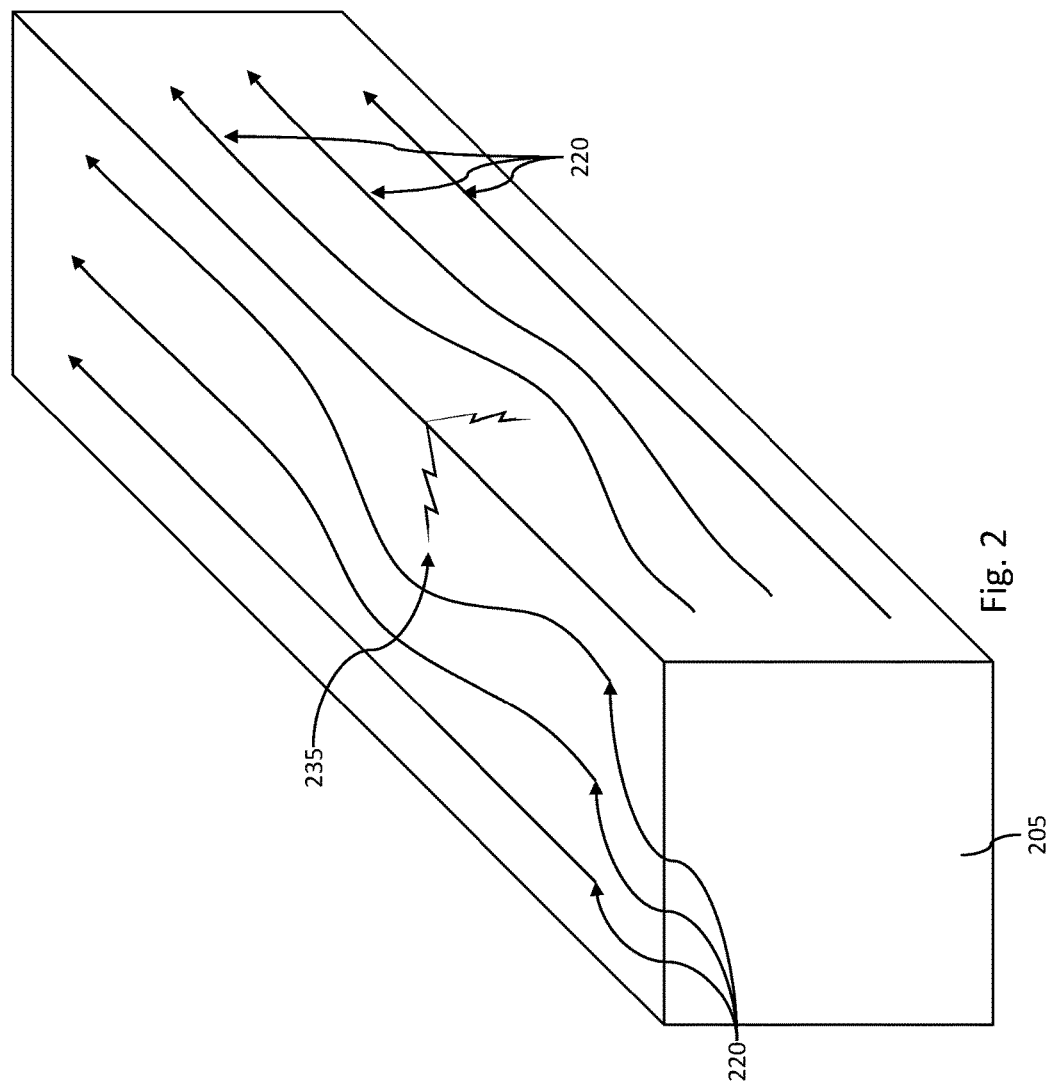

METHOD FOR DETECTING DEFECTS IN CONDUCTIVE MATERIALS BASED ON DIFFERENCES IN MAGNETIC FIELD CHARACTERISTICS MEASURED ALONG THE CONDUCTIVE MATERIALS

CROSS-REFERENCE TO RELATED APPLICATIONS

The present application claims priority to U.S. Application No. 62/277,657, filed Jan. 12, 2016, titled "DETECTING DISCONTINUITIES IN MAGNETICALLY CONDUCTIVE OBJECTS," which is incorporated by reference herein in its entirety.

TECHNICAL FIELD

The present disclosure relates, in general, to detecting defects. More particularly, the present disclosure relates to using a magnetometer to detect defects in conductive materials.

BACKGROUND

The following description is provided to assist the understanding of the reader. None of the information provided or references cited is admitted to be prior art. Physical objects can become damaged or deformed over time caused by normal wear and tear, accidents, sabotage, etc. If undetected and not corrected, such damage or deformities can cause system failures that can be expensive and/or dangerous. The ability to detect deformities in equipment can prevent accidents, save money, and protect lives.

SUMMARY

An illustrative method includes passing a magnetometer along a length of a material. The method may also include measuring, via the magnetometer, a first magnetic field magnitude along a first portion of the length of the material and measuring, via the magnetometer, a second magnetic field magnitude along a second portion of the length of material. In some examples, the first magnetic field magnitude and the second magnetic field magnitude are measured at a 10,000 Hertz (Hz) bandwidth. In other examples, the first magnetic field magnitude and the second magnetic field magnitude are measured at a 50,000 Hertz (Hz) bandwidth. The method may further include determining that the material comprises a defect along the second portion of the length of material by determining that the first magnetic field magnitude is different than the second magnetic field magnitude.

An illustrative method includes receiving, from a magnetometer, an initial magnetic field magnitude and moving the magnetometer parallel to a length of a material. The method may also include receiving, from the magnetometer, a measured magnetic field magnitude that is different than the initial magnetic field magnitude at a first location along the length of the material. The method may further include determining, based on the measured magnetic field magnitude, that the material comprises a defect at the first location.

An illustrative method includes measuring, using a magnetometer, a magnetic field of Earth while the magnetometer travels parallel to a length of material. The method may further include monitoring for a change in the measured magnetic field of Earth while the magnetometer travels parallel to the length of the material. The method may also include determining that a portion of the length of the material comprises a defect by detecting the change in the measured magnetic field of Earth.

An illustrative method includes inducing a current in a length of material and determining an expected magnitude of a magnetic field along the length of the material. The method may also include measuring, using a magnetometer, a measured magnitude of the magnetic field along at least a portion of the length of the material. The method may further include determining that the length of the material comprises a defect by comparing the expected magnitude of the magnetic field and the measured magnitude of the magnetic field.

An illustrative device includes a magnetometer configured to sense a magnetic field magnitude and a processor operatively coupled to the magnetometer. The processor may be configured to monitor the magnetic field magnitude sensed by the magnetometer. The processor may be also configured to determine a change in the magnetic field sensed by the magnetometer and to determine that a length of a material comprises a defect based at least on the change in the magnetic field.

An illustrative device includes a magnetometer configured to sense a magnetic field magnitude and a processor operatively coupled to the magnetometer. The processor may be configured to receive, from the magnetometer, a first magnetic field magnitude along a first portion of a length of material and to receive, from the magnetometer, a second magnetic field magnitude along a second portion of the length of material. The processor may be also configured to determine that the material comprises a defect along the second portion of the length of material by determining that the first magnetic field magnitude is different than the second magnetic field magnitude.

An illustrative device includes a magnetometer configured to sense a magnetic field magnitude and a processor operatively coupled to the magnetometer. The processor may be configured to determine an expected magnitude of a magnetic field along a length of a material. The processor may further configured to measure, using a magnetometer, a measured magnitude of the magnetic field along at least a portion of the length of the material and to determine that the length of the material comprises a defect by comparing the expected magnitude of the magnetic field and the measured magnitude of the magnetic field.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

FIG. 2 illustrates current paths through a conductor with a deformity in accordance with an illustrative embodiment.

Figure 1A:
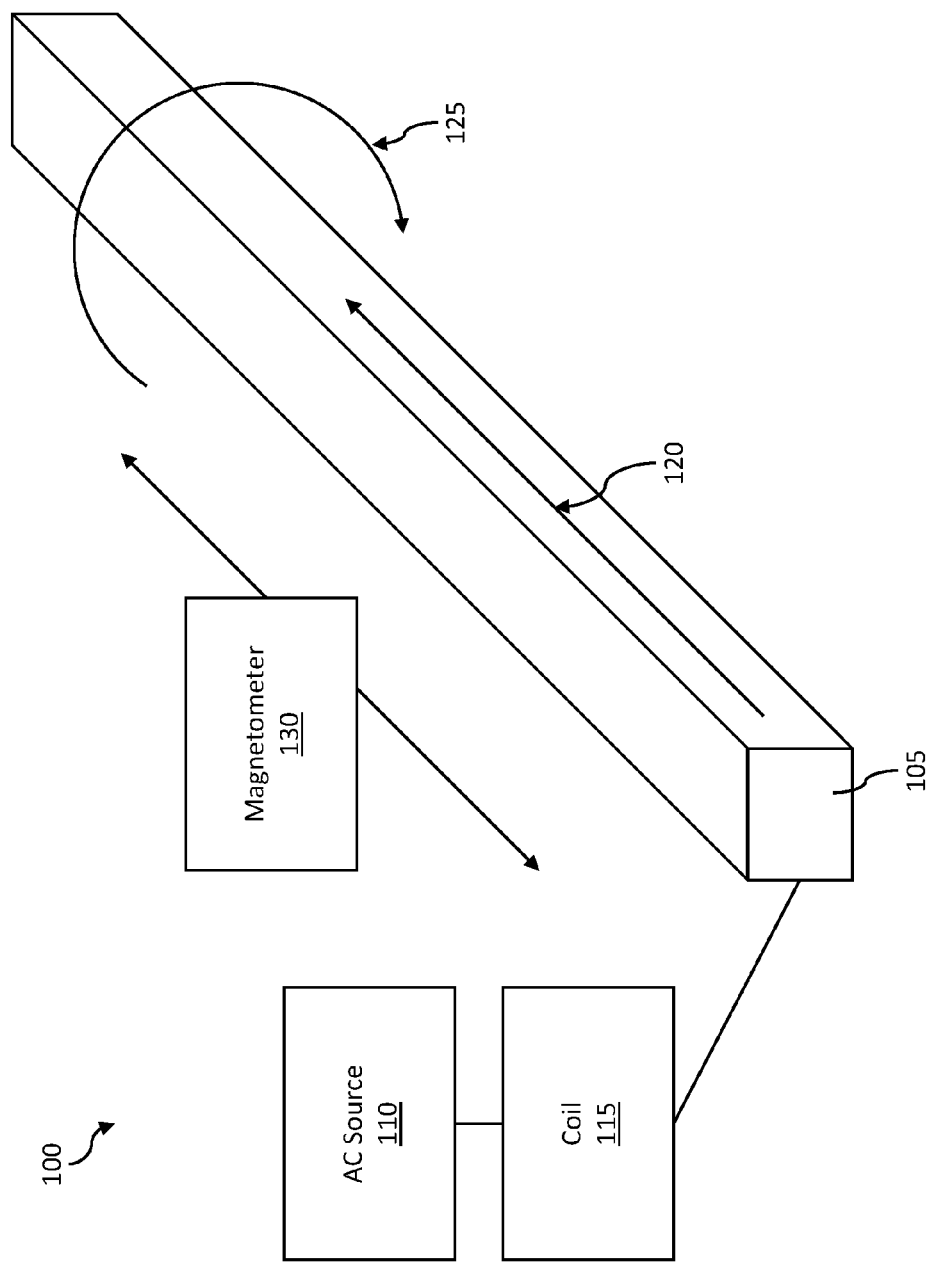
FIGS. 1A and 1B are block diagrams of a system for detecting deformities in a material in accordance with an illustrative embodiment.

The foregoing and other features of the present disclosure will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Nitrogen-vacancy centers (NV centers) are defects in a diamond's crystal structure, which can purposefully be manufactured in synthetic diamonds. In general, when excited by green light and microwave radiation, the NV centers cause the diamond to generate red light. When an excited NV center diamond is exposed to an external magnetic field the frequency of the microwave radiation at which the diamond generates red light and the intensity of the light change. By measuring the changes, the NV centers can be used to accurately detect the magnetic field strength.

In various embodiments described in greater detail below, a magnetometer using one or more diamonds with NV centers can be used to detect defects in conductive materials. According to Ampere's law, an electrical current through a conductor generates a magnetic field along the length of the conductor. Similarly, a magnetic field can induce a current through a conductor. In general, a conductor with continuous uniformity in size, shape, and material through which an electrical current passes will generate a continuous magnetic field along the length of the conductor. On the other hand, the same conductor but with a deformity or defect such as a crack, a break, a misshapen portion, holes, pits, gouges, impurities, anomalies, etc. will not generate a continuous magnetic field along the length of the conductor. For example, the area surrounding the deformity may have a different magnetic field than areas surrounding portions of the conductor without the deformity. In some deformities, such as a break in the conductor, the magnetic field on one side of the break may be different than the magnetic field on the other side of the break.

For example, a rail of railroad tracks may be checked for deformities using a magnetometer. A current can be induced in the rail, and the current generates a magnetic field around the rail. The magnetometer can be used by passing the magnetometer along the length of the rail, or along a portion of the rail. The magnetometer can be at the same location with respect to the central axis of the rail as the magnetometer passes along the length of the rail. The magnetometer detects the magnetic field along the length of the rail.

In some embodiments, the detected magnetic field can be compared to an expected magnetic field. If the detected magnetic field is different than the expected magnetic field, it can be determined that a defect exits in the rail. In some embodiments, the detected magnetic field along the length of the rail can be checked for areas that have a magnetic field that is different than the majority of the rail. It can be determined that the area that has a magnetic field that is different than the majority of the rail is associated with a defect in the rail.

The principles explained above can be applied to many scenarios other than checking the rails of railroad tracks. A magnetometer can be used to detect deformities in any suitable conductive material. For example, a magnetometer can be used to detect deformities in machinery parts such as turbine blades, wheels, engine components.

Figure 1B:
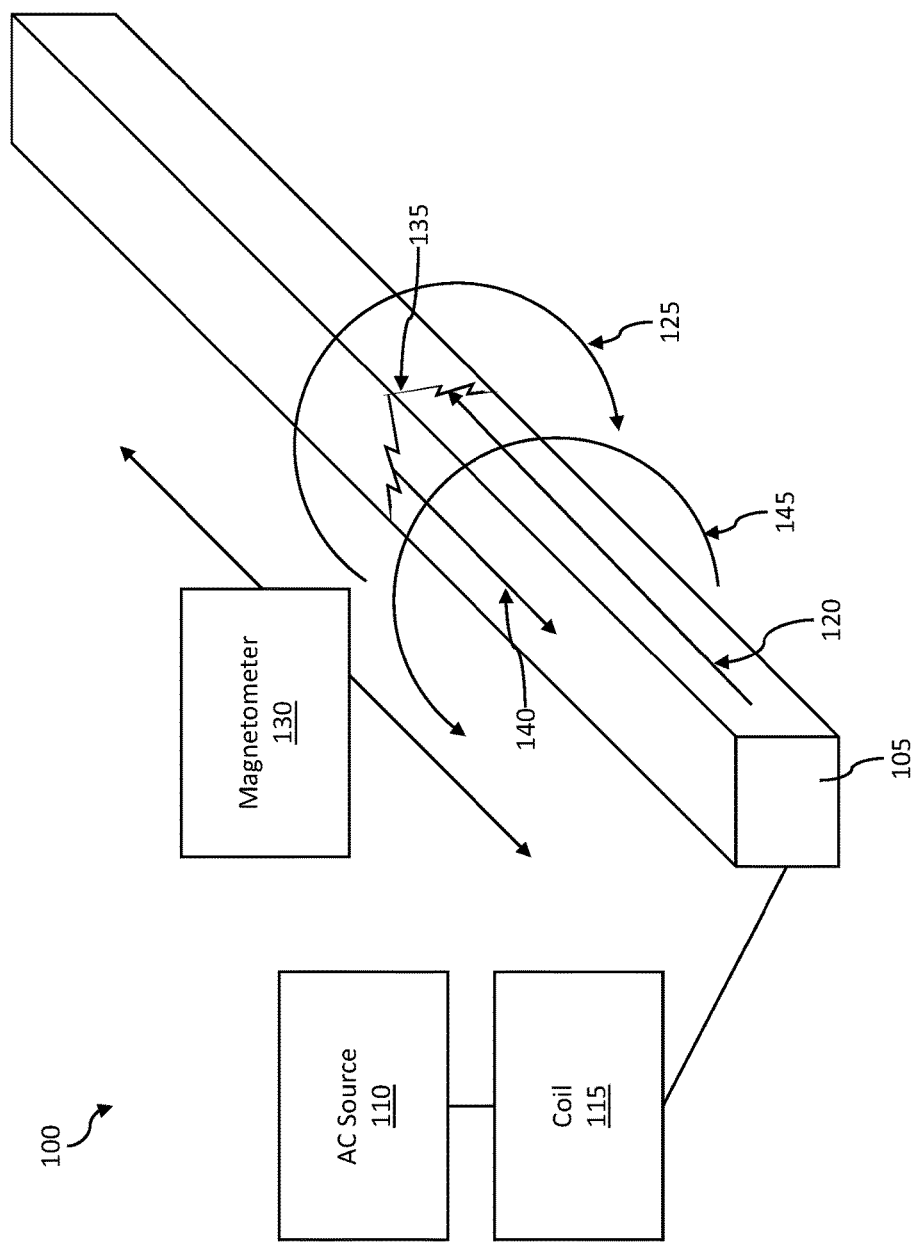

FIGS. 1A and 1B are block diagrams of a system for detecting deformities in a material in accordance with an illustrative embodiment. An illustrative system 100 includes a conductor 105, an alternating current (AC) source 110, a coil 115, and a magnetometer 130. In alternative embodiments, additional, fewer, and/or different elements may be used.

The conductor 105 is a length of conductive material. In some embodiments, the conductor 105 is paramagnetic. In some embodiments, the conductor 105 is ferromagnetic. In some embodiments, the conductor 105 is made of a ferrous material. The conductor 105 can be any suitable length and have any suitable cross-sectional shape.

A current indicated by the arrow labeled 120 in FIGS. 1A and 1B illustrates the direction of an induced current through the conductor 105. In the embodiments illustrated in FIGS. 1A and 1B, the AC source 110 and the coil 115 induce the induced current 120. For example, current from the AC source 110 can pass through the coil 115, thereby creating a magnetic field around the coil 115. The magnetic field of the coil 115 can be placed sufficiently close to the conductor 105 to create the induced current 120. The induced current 120 travels in a direction along the conductor 105 that is away from the coil 115. In alternative embodiments, any suitable system can be used to create the induced current 120.

In the embodiments illustrated in FIGS. 1A and 1B, an AC source 110 is used to provide power to the coil 115. The AC source 110 can be any suitable alternating current source. For example, power lines or traditional methods of obtaining alternating current power can be used. In another example, a third rail of a railway that is used to provide power to railcars can be used as the AC source 110. In yet another example, a crossing gate trigger of a railway can be used as the AC source 110.

In an illustrative embodiment, the induced current 120 is an alternating current. In some embodiments, the frequency of the induced current 120 can be altered. The magnetic field generated by the induced current 120 can change based on the frequency of the induced current 120. Thus, by using different frequencies, different features of the conductor 120 can be determined by measuring the magnetic field generated by the different frequencies, as explained in greater detail below. For example, a rapid sequence of different frequencies can be used. In another example, multiple frequencies can be applied at once and the resulting magnetic field can be demodulated. For example, the spatial shape and pattern of the vector magnetic field generated by eddy currents around the defect or imperfection changes with the frequency of the applied excitation field. A three-dimensional Cartesian magnetic field pattern around the defect or imperfection can be measured and imaged at one frequency at a time. The detected magnetic field pattern can be stored (e.g., in a digital medium or a continuous analog medium). The detected magnetic field pattern can be compared to previously measured images to generate a likely taxonomy or identification of the nature of the defect or imperfection and/or the location of the defect or imperfection.

The induced current 120 that passes through the conductor 105 generates a magnetic field. The magnetic field has a direction around the conductor 105 indicated by the arrow labeled with numeral 125. The magnetometer 130 can be passed along the length of the conductor 105. FIGS. 1A and 1B include an arrow parallel to the length of the conductor 105 indicating the path of the magnetometer 130. In alternative embodiments, any suitable path may be used. For example, in embodiments in which the conductor 105 is curved (e.g., as a railroad rail around a corner), the magnetometer 130 can follow the curvature of the conductor 105.

The magnetometer 130 can measure the magnitude and/or direction of magnetic field vectors along the length of the conductor 105. For example, the magnetometer 130 measures the magnitude and the direction of the magnetic field at multiple sample points along the length of the conductor 105 at the same orientation to the conductor 105 at the sample points. For instance, the magnetometer 130 can pass along the length of the conductor 105 while above the conductor 105.

Any suitable magnetometer can be used as the magnetometer 130. In some embodiments, the magnetometer uses one or more diamonds with NV centers. The magnetometer 130 can have a sensitivity suitable for detecting changes in the magnetic field around the conductor 105 caused by deformities. In some instances, a relatively insensitive magnetometer 130 may be used. In such instances, the magnetic field surrounding the conductor 105 should be relatively strong. In some such instances, the current required to pass through the conductor 105 to create a relatively strong magnetic field may be impractical or dangerous. Thus, for example, the magnetometer 130 can have a sensitivity of about $10^{-9}$ Tesla (one nano-Tesla) and can detect defects at a distance of about one to ten meters away from the conductor 105. In such an example, the conductor 105 can be a steel pipe with a diameter of 0.2 meters. In one example, the current through the conductor 105 may be about one Ampere (Amp), and the magnetometer 130 may be about one meter away from the conductor 105. In another example, the current through the conductor 105 may be about one hundred Amps, and the magnetometer 130 may be about ten meters away. The magnetometer 130 can have any suitable measurement rate. In an illustrative embodiment, the magnetometer 130 can measure the magnitude and/or the direction of a magnetic field at a particular point in space up to one million times per second. For example, the magnetometer 130 can take one hundred, one thousand, ten thousand, or fifty thousand times per second.

In embodiments in which the magnetometer 130 measures the direction of the magnetic field, the orientation of the magnetometer 130 to the conductor 105 can be maintained along the length of the conductor 105. As the magnetometer 130 passes along the length of the conductor 105, the direction of the magnetic field can be monitored. If the direction of the magnetic field changes or is different than an expected value, it can be determined that a deformity exits in the conductor 105.

In such embodiments, the magnetometer 130 can be maintained at the same orientation to the conductor 105 because even if the magnetic field around the conductor 105 is uniform along the length of the conductor 105, the direction of the magnetic field is different at different points around the conductor 105. For example, referring to the induced current magnetic field direction 125 of FIG. 1A, the direction of the magnetic field above the conductor 105 is pointing to the right-hand side of the figure (e.g., according to the "right-hand rule"). The direction of the magnetic field below the conductor 105 is pointing to the left-hand side of the figure. Similarly, the direction of the magnetic field is down at a point that is to the right of the conductor 105. Following the same principle, the direction of the magnetic field is up at a point that is to the left of the conductor 105. Therefore, if the induced current 120 is maintained at the same orientation to the conductor 105 along the length of the conductor 105 (e.g., above the conductor 105, below the conductor 105, twelve degrees to the right of being above the conductor 105, etc.), the direction of the magnetic field can be expected to be the same or substantially similar along the length of the conductor 105. In some embodiments, the characteristics of the induced current 120 can be known (e.g., Amps, frequency, etc.) and the magnitude and direction of the magnetic field around the conductor 105 can be calculated.

In embodiments in which the magnetometer 130 measures magnitude of the magnetic field and not the direction of the magnetic field, the magnetometer 130 can be located at any suitable location around the conductor 105 along the length of the conductor 105, and the magnetometer 130 may not be held at the same orientation along the length of the conductor 105. In such embodiments, the magnetometer 130 may be maintained at the same distance from the conductor 105 along the length of the conductor 105 (e.g., assuming the same material such as air is between the magnetometer 130 and the conductor 105 along the length of the conductor 105).

FIG. 1A illustrates the system 100 in which the conductor 105 does not contain a deformity. FIG. 1B illustrate the system 100 in which the conductor 105 includes a break 135. As shown in FIG. 1B, a portion of the induced current 120 is reflected back from the break 135 as shown by the reflected current 140. As in FIG. 1B, the induced current magnetic field direction 125 corresponds to the induced current 120. The reflected current magnetic field direction 145 corresponds to the reflected current 140. The induced current magnetic field direction 125 is opposite the reflected current magnetic field direction 145 because the induced current 120 travels in the opposite direction from the reflected current 140.

In some embodiments in which the break 135 is a full break that breaks conductivity between the portions of the conductor 105, the magnitude of the induced current 120 may be equal to or substantially similar to the reflected current 140. Thus, the combined magnetic field around the conductor 105 will be zero or substantially zero. That is, the magnetic field generated by the induced current 120 is canceled out by the equal but opposite magnetic field generated by the reflected current 140. In such embodiments, the break 135 may be detected using the magnetometer 130 by comparing the measured magnetic field, which is substantially zero, to an expected magnetic field, which is a non-zero amount. As the magnetometer 130 travels closer to the break 135, the magnitude of the detected magnetic field reduces. In some embodiments, it can be determined that the break 135 exists when the measured magnetic field is below a threshold value. In some embodiments, the threshold value may be a percentage of the expected value, such as ±0.1%, ±1%, ±5%, ±10%, ±15%, ±50%, or any other suitable portion of the expected value. In alternative embodiments, any suitable threshold value may be used.

In embodiments in which the break 135 allows some of the induced current 120 to pass through or around the break 135, the magnitude of the reflected current 140 is less than the magnitude of the induced current 120. Accordingly, the magnitude of the magnetic field generated by the reflected current 140 is less than the magnitude of the magnetic field generated by the induced current 120. Although the magnitudes of the induced current 120 and the reflected current 140 may not be equal, the induced current magnetic field direction 125 and the reflected current magnetic field direction 145 are still opposite. Thus, the net magnetic field is a magnetic field in the induced current magnetic field direction 125. The magnitude of the net magnetic field is the magnitude of the magnetic field generated by the induced current 120 minus the magnitude of the magnetic field generated by the reflected current 140. As mentioned above, the magnetic field measured by the magnetometer 130 can be compared against a threshold value. Depending upon the severity, size, and/or shape of the break 135, the net magnetic field sensed by the magnetometer 130 may or may not be less than or greater than the threshold value. Thus, the threshold value can be adjusted to adjust the sensitivity of the system. That is, the more that the threshold value deviates from the expected value, the more severe the deformity in the conductor 105 is to cause the magnitude of the sensed magnetic field to be less than the threshold value. Thus, the smaller the threshold value is, the finer, smaller, less severe, etc. deformities are that are detected by the system 100.

As mentioned above, the direction of the magnetic field around the conductor 105 can be used to sense a deformity in the conductor 105. FIG. 2 illustrates current paths through a conductor with a deformity in accordance with an illustrative embodiment. FIG. 2 is meant to be illustrative and explanatory only and not meant to be limiting with respect to the functioning of the system.

A current can be passed through the conductor 205, as discussed above with regard to the conductor 105. The current paths 220 illustrate the direction of the current. As shown in FIG. 2, the conductor 205 includes a deformity 235. The deformity 235 can be any suitable deformity, such as a crack, a dent, an impurity, etc. The current passing through the conductor 205 spreads uniformly around the conductor 205 in portions that do not include the deformity 235. In some instances, the current may be more concentrated at the surface of the conductor 205 than at the center of the conductor 205.

In some embodiments, the deformity 235 is a portion of the conductor 205 that does not allow or resists the flow of electrical current. Thus, the current passing through the conductor 205 flows around the deformity 235. As shown in FIG. 1A, the induced current magnetic field direction 125 is perpendicular to the direction of the induced current 120. Thus, as in FIG. 1A, when the conductor 105 does not include a deformity, the direction of the magnetic field around the conductor 105 is perpendicular to the length of the conductor 105 all along the length of the conductor 105.

As shown in FIG. 2, when the conductor 205 includes a deformity 235 around which the current flows, the direction of the current changes, as shown by the current paths 220. Thus, even though the conductor 205 is straight, the current flowing around the deformity 235 is not parallel to the length of the conductor 205. Accordingly, the magnetic field generated by the current paths corresponding to the curved current paths 220 is not perpendicular to the length of the conductor 205. Thus, as a magnetometer such as the magnetometer 130 passes along the length of the conductor 205, a change in direction of the magnetic field around the conductor 205 can indicate that the deformity 235 exits. As the magnetometer 130 approaches the deformity 235, the direction of the magnetic field around the conductor 205 changes from being perpendicular to the length of the conductor 205. As the magnetometer 130 passes along the deformity 235, the change in direction of the magnetic field peaks and then decreases as the magnetometer 130 moves away from the deformity 235. The change in direction of the magnetic field can indicate the location of the deformity 235. In some instances, the conductor may have a deformity that reflects a portion of the current, as illustrated in FIG. 1B, and that deflects the flow of the current, as illustrated in FIG. 2.

The size, shape, type, etc. of the deformity 235 determines the spatial direction of the magnetic field surrounding the deformity 235. In some embodiments, multiple samples of the magnetic field around the deformity 235 can be taken to create a map of the magnetic field. In an illustrative embodiment, each of the samples includes a magnitude and direction of the magnetic field. Based on the spatial shape of the magnetic field surrounding the deformity 235, one or more characteristics of the deformity 235 can be determined, such as the size, shape, type, etc. of the deformity 235. For instance, depending upon the map of the magnetic field, it can be determined whether the deformity 235 is a dent, a crack, an impurity in the conductor, etc. In some embodiments, the map of the magnetic field surrounding the deformity 235 can be compared to a database of known deformities. In an illustrative embodiment, it can be determined that the deformity 235 is similar to or the same as the closest matching deformity from the database. In an alternative embodiment, it can be determined that the deformity 235 is similar to or the same as a deformity from the database that has a similarity score that is above a threshold score. The similarity score can be any suitable score that measures the similarity between the measured magnetic field and one or more known magnetic fields of the database.

A magnetometer can be used to detect defects in conductive materials in many different situations. In one example, a magnetometer can be used to detect defects in railroad rails. In such an example, a railroad car can be located along the rails and travel along the tracks. A magnetometer can be located on the car a suitable distance from the rails, and monitor the magnetic field around one or more of the rails as the car travels along the tracks. In such an example, the current can be induced in one or more of the rails at a known stationary location. In an alternative embodiment, the coil that induces the current in the rails can be located on the moving car and can move with the magnetometer.

In such an example, the magnetometer can be located on a typical rail car or a specialized rail car device. The magnetometer can be mounted and/or the rail car can be designed in a manner that maintains the orientation of the magnetometer with respect to one or more of the rails. In some instances, it may not be feasible to maintain perfect orientation of the magnetometer with the rails because of, for example, bumps or dips in the terrain, movement of people or cargo in the car, imperfections in the rails, etc. In such instances, one or more gyroscopes can be used to track the relative position of the magnetometer to the one or more rails. In alternative embodiments, any suitable system can be used to track the relative position of the magnetometer, such as sonar, lasers, or accelerometers. The system may use the change in relative position to adjust the magnitude and/or direction of the expected magnetic field accordingly.

In another example, the magnetometer can be used to detect deformities in pipes. In some instances, the pipes can be buried or may be beneath water. In scenarios in which the conductor being checked for deformities is surrounded by a relatively conductive material, such as water, the magnetometer can be placed relatively close to the coil inducing the current in the conductor. Because the conductor is surrounded by the relatively conductive material, the strength of the current traveling through the conductor will diminish much quicker the further away from the coil the magnetometer is compared to the conductor being surrounded by a relatively non-conductive material, such as air. In such conditions, the coil can travel along the conductor with the magnetometer. The magnetometer and the coil can be separated enough that the magnetic field from the coil does not cause excessive interference with the magnetometer.

In some instances, a magnetometer can be used to detect leaks in pipes. For example, some fluids that are transported via a pipeline have magnetic properties. In such instances, the fluid and/or the pipe can be magnetized. The magnetometer (e.g., an array of magnetometers) can travel along the pipe to detect discrepancies in the detected magnetic field around the pipe as explained above. Differences or changes in the magnetic field can be caused by the fluid leaking from the pipe. Thus, detecting a difference or change in the magnetic field using the magnetometer can indicate a leak in the pipe. For example, a stream or jet of fluid or gas flowing from a pipe can be detected by a magnetic field around the stream or jet. In some embodiments, the volumetric leak rate can be determined based on the magnetic field (e.g., the size of the magnetic field). The leak rate can be used, for example, to prioritize remediation of leaks.

In some embodiments, a current may not be induced in the conductor. In such embodiments, any suitable magnetic field may be detected by the magnetometer. For example, the earth generates a magnetic field. The material being inspected may deflect or otherwise affect the earth's magnetic field. If the inspected material is continuous, the deflection of the earth's magnetic field is the same or similar along the length of the material. However, if there is a deformity or defect, the deflection of the earth's magnetic field will be different around the deformity or defect.

In some embodiments, any other suitable magnetic source may be used. For example, a source magnet may be applied to a material that is paramagnetic. The magnetic field around the paramagnetic material can be used to detect deformities in the material using principles explained herein. In such an embodiment, the magnetometer can be located relatively close to the source magnet.

As mentioned above, in some embodiments the measured magnetic field is compared to an expected magnetic field. The expected magnetic field can be determined in any suitable manner. The following description is one example of how the expected magnetic field can be determined.

In embodiments in which a coil is used to induce a current in the conductor (e.g., the embodiments illustrated in FIGS. 1A and 1B), the magnitude of the magnetic field of the coil at the conductor, $B^{coil}$, can be determined using equation (1):

$$B^{coil} = \frac{\mu I}{4\pi} \int \frac{dl_{coil} \cdot r_{cr}}{r_{cr}^2} \qquad (1)$$

In equation (1), $\mu$ is the magnetic permeability (Newtons/Amp$^2$) of the medium between the coil and the conductor (e.g., conductor 105), I is the current through the coil (Amps), $dl_{coil}$ is the elemental length of the coil wire (meters), and $r_{cr}$ is the scalar distance from the coil to the rail (meters). It will be understood that he magnitude of the magnetic field of the coil of equation (1) can be converted into a vector quantity with a circular profile symmetric about the coil center of alignment and, therefore, circumferentially constant with a radial relationship consistent with equation (1).

The forward current in the rail, $I^{rail}$, can be calculated using equation (2):

$$I^{rail} = \alpha \beta^{coil} \qquad (2)$$

In equation (2), $\alpha$ is the magnetic susceptibility of the conductor (Henry).

The magnitude of the magnetic field of the rail magnetic B-field is:

$$B^{rail} = \frac{\mu I^{rail}}{4\pi} \int \frac{dl_{rail} \cdot r_{rm}}{r_{rm}^2} \qquad (3)$$

In equation (3), $r_{rm}$ is the distance from the rail to the magnetometer, and $dl_{rail}$ is the length of the rail from the location the magnetic field from the coil interacts with the rail and the location of the magnetometer (meters).

In some embodiments, the magnetometer can measure the magnitude of a magnetic field in one or more directions. For example, the magnetometer can measure the magnitude of the magnetic field in three orthogonal directions: x, y, and z. Equation (4) shows the relationship between the measured magnitudes of the detected magnetic field in the x, y, and z directions ($B_x$, $B_y$, and $B_z$, respectively) and the vector of the magnetic field measured by the magnetometer ($B^{meas}$) (e.g., using a dipole model):

$$B^{meas} = \begin{bmatrix} B_x \\ B_y \\ B_z \end{bmatrix} \qquad (4)$$

If the rail is uniform and homogeneous, then $B^{meas}$ is essentially equal to $B^{rail}$. When a defect, anomaly, deformity, etc. is present within the rail, the measured magnetic vector, $B^{meas}$, is different from the expected magnetic field of the rail, $B^{rail}$, by a function of translation ($F_t$) because of the anomaly, as shown in equation (5):

$$B^{meas} = F_t B^{rail} \qquad (5)$$

A linear expansion of the translation function allows an algebraic formula isolating position, $\delta$, changes caused by the rail anomaly to be detected from a difference between the reference and measured field as follows:

$$\delta B^{meas} = +\frac{\partial F_t}{\partial P} \delta B^{rail} \qquad (6)$$

$$B^{meas} = (I_{rail} + \delta) B^{rail} \qquad (7)$$

$$B^{meas} - B^{rail} = \delta B^{rail} \qquad (8)$$

therefore, $$[(B^{meas} - B^{rail})_k (B^{meas} - B^{rail})_{k+1} \ldots ] = [\delta] \cdot [(B^{rail})_k (B^{rail})_{k+1} \ldots ] \qquad (9)$$

In equations (6)-(9), $\delta$ is the distance of the deformity along the conductor from the magnetometer, $I_{rail}$ is the current through the conductor, and k denotes a particular measurement sample. In an illustrative embodiment, one hundred samples are taken. In alternative embodiments, more or fewer than one hundred samples are taken. When processed through a Fast Fourier Transform algorithm (or any other suitable algorithm), noise may be suppressed and echoes or uneven departures from the reference field ($B^{rail}$) are correlated to the rail break at a known position and orientation relative to the magnetometer at distance $\delta$ according to the following equations:

$$[\delta] = \frac{[(B^{meas} - B^{rail})_k (B^{meas} - B^{rail})_{k+1} \cdots ]}{[(B^{rail})_k (B^{rail})_{k+1} \cdots ]} \quad (10)$$

$$\Im[\delta] = \Im(j\omega, X) \quad (11)$$

Using the equations above, the distance from the magnetometer to the deformation can be determined based on the current induced in the conductor (I) and the measured magnetic field at a particular distance from the conductor.

In the embodiments illustrated in FIGS. 1A and 1B, one magnetometer 130 is used to pass along the length of the conductor 105 to monitor for deformities. In alternative embodiments, two or more magnetometers 130 may be used. The multiple magnetometers 130 can be oriented around the conductor 105 in any suitable manner. Using multiple magnetometers 130 provides benefits in some instances. For example, using multiple magnetometers 130 provides multiple sample points simultaneously around the conductor 105. In some instances, the multiple sample points can be redundant and can be used to check the accuracy of the samples. In some instances, having multiple sample points spread around a conductor 105 increases the chances that there is a magnetometer 130 at a point around the conductor 105 that has the greatest angle of departure. That is, sampling multiple points around the conductor 105 increases the chances that a magnetometer 130 will detect an anomaly in the conductor 105 based on the greatest change in the magnetic field around the conductor 105.

Figure 3:
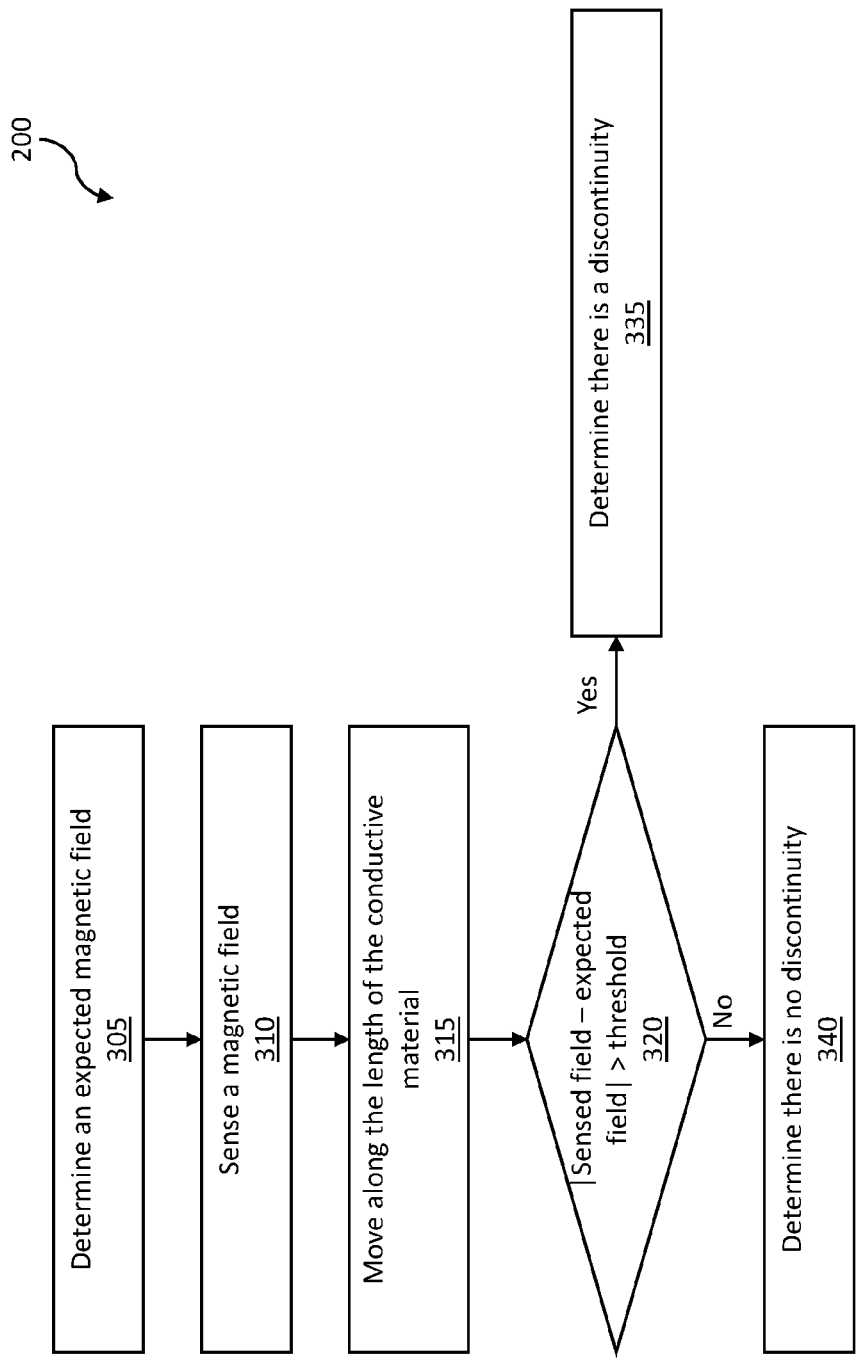
FIG. 3 is a flow diagram of a method for detecting deformities in accordance with an illustrative embodiment.

FIG. 3 is a flow diagram of a method for detecting deformities in accordance with an illustrative embodiment. In alternative embodiments, additional, fewer, or different operations may be performed. Also, the use of a flow chart and/or arrows is not meant to be limiting with respect to the order or flow of operations. For example, in some embodiments, two or more of the operations may be performed simultaneously.

In an operation 305, an expected magnetic field is determined. In an illustrative embodiment, the expected magnetic field can include a magnitude and a direction (e.g., be a vector). In alternative embodiments, the expected magnetic field includes a magnitude or a direction. In an illustrative embodiment, the expected magnetic field is determined based on a current induced in a conductor. For example, a power source and a coil can be used to induce a current in a conductor. Based on the current through the coil and the distance between the coil and the conductor (and any other suitable variable), the induced current through the conductor can be calculated. The location of the coil with respect to the magnetometer can be known, and, therefore, the direction of the induced current can be known. If the current through the conductor is known or calculated, the magnetic field at a point around the conductor can be calculated. Thus, the magnetic field at the point around the conductor that the magnetometer is can be calculated based on the induced current, assuming that no deformity exits.

In an alternative embodiment, the expected magnetic field can be determined using a magnetometer. As discussed above, a deformity can be detected by detecting a change in a magnetic field around a conductor. In such embodiments, one or more initial measurements can be taken using the magnetometer. The one or more initial measurements can be used as the expected magnetic field. That is, if the conductor is not deformed along the length of the conductor, the magnetic field along the conductor will be the same as or substantially similar to the initial measurements. In alternative embodiments, any suitable method for determining an expected magnetic field can be used.

In an operation 310, a magnetic field is sensed. In an illustrative embodiment, a magnetometer is used to measure a magnetic field around a conductor along the length of the conductor. In an operation 315, the magnetometer moves along the length of the conductive material. The magnetometer can maintain an orientation to the conductor as the magnetometer travels along the length of the conductor. As the magnetometer moves along the length of the conductive material, the magnetometer can be used to gather multiple samples along the length of the conductive material.

In an operation 320, the difference between the sensed field and the expected field is compared to a threshold. In an illustrative embodiment, the absolute value of the difference between the sensed field and the expected field is compared to the threshold. In such an embodiment, the magnitude of the difference is used and not the sign of the value (e.g., negative values are treated as positive values). The threshold can be any suitable threshold value. For example, the difference between the magnitude of the sensed vector and the magnitude of the expected vector can be compared against a threshold magnitude value. In another example, the difference between the direction of the sensed vector and the direction of the expected vector can be compared against a threshold value. The threshold value can be chosen based on a desired level of sensitivity. The higher the threshold value is, the lower the sensitivity of the system is. For example, the threshold value for a difference in vector angles can be 5-10 micro radians. In alternative embodiments, the threshold value can be less than 5 micro radians or greater than 10 micro radians.

If the difference between the sensed field and the expected field is greater than the threshold, then it can be determined in an operation 335 that there is a defect. In alternative embodiments, a sufficiently large difference in the sensed field and the expected field can indicate an anomaly in the conductor, a deformity in the conductor, etc. If the difference between the sensed field and the expected field is not greater than the threshold, then it can be determined in an operation 340 that there is no defect. That is, if the sensed field is sufficiently close to the expected field, it can be determined that there is not a sufficiently large anomaly, break, deformity, etc. in the conductor.

Figure 4:
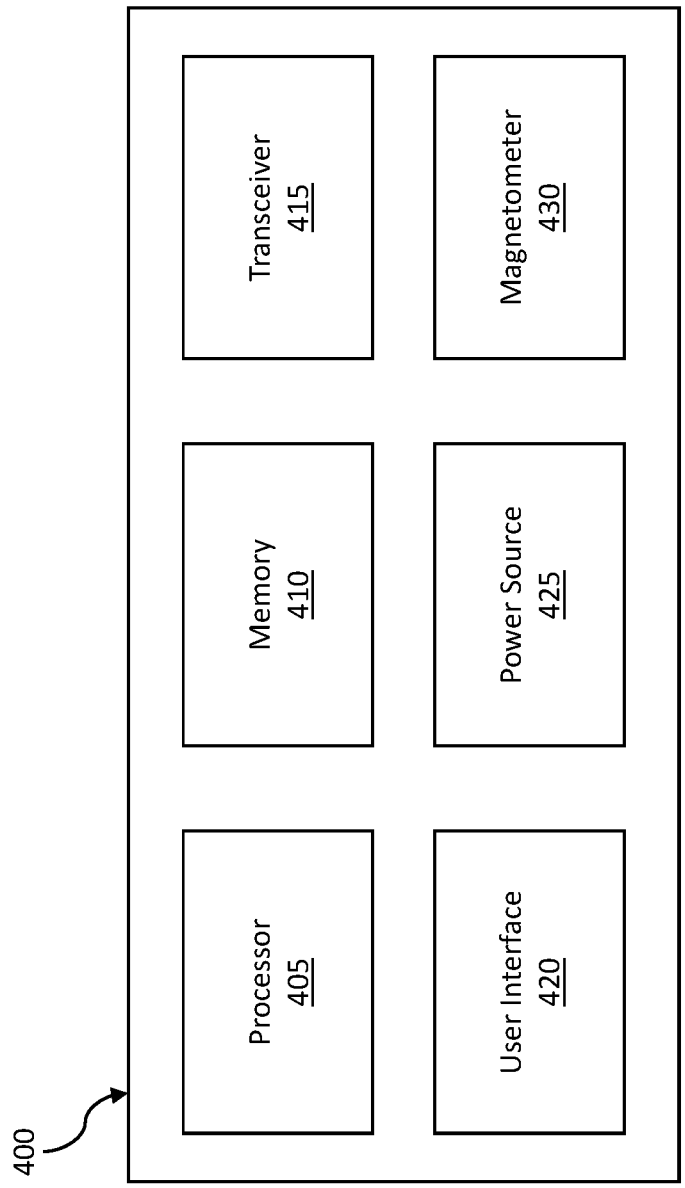
FIG. 4 is a block diagram of a computing device in accordance with an illustrative embodiment.

FIG. 4 is a block diagram of a computing device in accordance with an illustrative embodiment. An illustrative computing device 400 includes a memory 410, a processor 405, a transceiver 415, a user interface 420, a power source 425, and an magnetometer 430. In alternative embodiments, additional, fewer, and/or different elements may be used. The computing device 400 can be any suitable device described herein. For example, the computing device 400 can be a desktop computer, a laptop computer, a smartphone, a specialized computing device, etc. The computing device 400 can be used to implement one or more of the methods described herein.

In an illustrative embodiment, the memory 410 is an electronic holding place or storage for information so that the information can be accessed by the processor 405. The memory 410 can include, but is not limited to, any type of random access memory (RAM), any type of read only memory (ROM), any type of flash memory, etc. such as magnetic storage devices (e.g., hard disk, floppy disk, magnetic strips, etc.), optical disks (e.g., compact disk (CD), digital versatile disk (DVD), etc.), smart cards, flash memory devices, etc. The computing device 400 may have one or more computer-readable media that use the same or a different memory media technology. The computing device 400 may have one or more drives that support the loading of a memory medium such as a CD, a DVD, a flash memory card, etc.

In an illustrative embodiment, the processor 405 executes instructions. The instructions may be carried out by a special purpose computer, logic circuits, or hardware circuits. The processor 405 may be implemented in hardware, firmware, software, or any combination thereof. The term "execution" is, for example, the process of running an application or the carrying out of the operation called for by an instruction. The instructions may be written using one or more programming language, scripting language, assembly language, etc. The processor 405 executes an instruction, meaning that it performs the operations called for by that instruction. The processor 405 operably couples with the user interface 420, the transceiver 415, the memory 410, etc. to receive, to send, and to process information and to control the operations of the computing device 400. The processor 405 may retrieve a set of instructions from a permanent memory device such as a ROM device and copy the instructions in an executable form to a temporary memory device that is generally some form of RAM. An illustrative computing device 400 may include a plurality of processors that use the same or a different processing technology. In an illustrative embodiment, the instructions may be stored in memory 410.

In an illustrative embodiment, the transceiver 415 is configured to receive and/or transmit information. In some embodiments, the transceiver 415 communicates information via a wired connection, such as an Ethernet connection, one or more twisted pair wires, coaxial cables, fiber optic cables, etc. In some embodiments, the transceiver 415 communicates information via a wireless connection using microwaves, infrared waves, radio waves, spread spectrum technologies, satellites, etc. The transceiver 415 can be configured to communicate with another device using cellular networks, local area networks, wide area networks, the Internet, etc. In some embodiments, one or more of the elements of the computing device 400 communicate via wired or wireless communications. In some embodiments, the transceiver 415 provides an interface for presenting information from the computing device 400 to external systems, users, or memory. For example, the transceiver 415 may include an interface to a display, a printer, a speaker, etc. In an illustrative embodiment, the transceiver 415 may also include alarm/indicator lights, a network interface, a disk drive, a computer memory device, etc. In an illustrative embodiment, the transceiver 415 can receive information from external systems, users, memory, etc.

In an illustrative embodiment, the user interface 420 is configured to receive and/or provide information from/to a user. The user interface 420 can be any suitable user interface. The user interface 420 can be an interface for receiving user input and/or machine instructions for entry into the computing device 400. The user interface 420 may use various input technologies including, but not limited to, a keyboard, a stylus and/or touch screen, a mouse, a track ball, a keypad, a microphone, voice recognition, motion recognition, disk drives, remote controllers, input ports, one or more buttons, dials, joysticks, etc. to allow an external source, such as a user, to enter information into the computing device 400. The user interface 420 can be used to navigate menus, adjust options, adjust settings, adjust display, etc.

The user interface 420 can be configured to provide an interface for presenting information from the computing device 400 to external systems, users, memory, etc. For example, the user interface 420 can include an interface for a display, a printer, a speaker, alarm/indicator lights, a network interface, a disk drive, a computer memory device, etc. The user interface 420 can include a color display, a cathode-ray tube (CRT), a liquid crystal display (LCD), a plasma display, an organic light-emitting diode (OLED) display, etc.

In an illustrative embodiment, the power source 425 is configured to provide electrical power to one or more elements of the computing device 400. In some embodiments, the power source 425 includes an alternating power source, such as available line voltage (e.g., 120 Volts alternating current at 60 Hertz in the United States). The power source 425 can include one or more transformers, rectifiers, etc. to convert electrical power into power useable by the one or more elements of the computing device 400, such as 1.5 Volts, 8 Volts, 12 Volts, 24 Volts, etc. The power source 425 can include one or more batteries.

In an illustrative embodiment, the computing device 400 includes a magnetometer 430. In other embodiments, magnetometer 430 is an independent device and is not integrated into the computing device 400. The magnetometer 430 can be configured to measure magnetic fields. For example, the magnetometer 430 can be the magnetometer 100, the magnetometer 200, the magnetometer 300, or any suitable magnetometer. The magnetometer 430 can communicate with one or more of the other components of the computing device 400 such as the processor 405, the memory 410, etc. For example, one or more photo detectors of the magnetometer 430 can transmit a signal to the processor 405 indicating an amount of light detected by the photo detector. The signal can be used to determine the strength and/or direction of the magnetic field applied to the diamond of the magnetometer 430. In alternative embodiments, any suitable component of the magnetometer 430 can transmit a signal to other components of the computing device 400 (e.g., the processor 405), such as a Helmholtz coil, a source light photo detector, one or more modulated light photo detectors, a light source, etc.

In an illustrative embodiment, any of the operations described herein can be implemented at least in part as computer-readable instructions stored on a computer-readable memory. Upon execution of the computer-readable instructions by a processor, the computer-readable instructions can cause a node to perform the operations.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." Further, unless otherwise noted, the use of the words "approximate," "about," "around," "substantially," etc., mean plus or minus ten percent.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method comprising:
    passing a magnetometer along a length of a material;
    measuring, via the magnetometer, a first magnetic field magnitude along a first portion of the length of the material;
    measuring, via the magnetometer, a second magnetic field magnitude along a second portion of the length of material; and
    determining that the material comprises a defect along the second portion of the length of material by determining that the first magnetic field magnitude is different than the second magnetic field magnitude.

2. The method of claim 1, wherein said determining that the first magnetic field magnitude is different than the second magnetic field magnitude comprises determining that the first magnetic field magnitude is different than the second magnetic field magnitude by at least a first threshold.

3. The method of claim 1, wherein the first magnetic field magnitude and the second magnetic field magnitude are measured at a 10,000 Hertz (Hz) bandwidth.

4. The method of claim 1, wherein the first magnetic field magnitude and the second magnetic field magnitude are measured at a 50,000 Hertz (Hz) bandwidth.

5. The method of claim 1, wherein the first magnetic field magnitude and the second magnetic field magnitude are measured at a sensitivity of $10^{-9}$ Tesla.

6. The method of claim 1, wherein said measuring the first magnetic field magnitude comprises measuring the first magnetic field magnitude in three directions.

7. The method of claim 6, wherein each of the three directions are orthogonal to one another.

8. The method of claim 1, wherein said passing the magnetometer along the length of the material comprises maintaining a consistent distance between the magnetometer and the length of the material.

9. The method of claim 8, wherein the consistent distance is a distance between five and ten meters.

10. The method of claim 1, wherein the material is a ferrous material.

11. The method of claim 1, wherein the material is ferromagnetic.

12. The method of claim 1, wherein the material comprises at least one of a railway rail or a pipe.

13. The method of claim 1, wherein the material comprises a component of machinery.

14. The method of claim 1, wherein the defect comprises a break, a crack, a hole, a pit, or a gouge in the length of the material.

15. The method of claim 1, further comprising passing a second magnetometer along the length of the material,
    wherein the magnetometer and the second magnetometer are configured to measure a magnetic field at different locations simultaneously.

* * * * *